(12) United States Patent
Nottet

(10) Patent No.: US 6,787,573 B2
(45) Date of Patent: Sep. 7, 2004

(54) ANTIVIRAL THERAPY

(75) Inventor: Johannes Servatius Leonardus Maria Nottet, Amsterdam (NL)

(73) Assignees: Universiteit Utrecht, Utrecht (NL); Universitair Medisch Centrum Utrecht, Utrecht (NL)

( * ) Notice: Subject to any disclaimer, the term of this patent is extended or adjusted under 35 U.S.C. 154(b) by 0 days.

(21) Appl. No.: 10/099,542

(22) Filed: Mar. 14, 2002

(65) Prior Publication Data

US 2003/0171441 A1 Sep. 11, 2003

Related U.S. Application Data

(63) Continuation-in-part of application No. 09/608,716, filed on Jun. 30, 2002, now Pat. No. 6,387,959.
(60) Provisional application No. 60/142,297, filed on Jul. 2, 1999.

(51) Int. Cl.[7] .................. A61K 31/10; A61K 31/045; A61K 31/075; A61K 31/21; A61K 31/185
(52) U.S. Cl. .................. 514/708; 514/709; 514/717; 514/713; 514/730; 514/506; 514/576; 514/544
(58) Field of Search .................. 514/713, 576, 514/506, 544, 708, 709, 717, 730

(56) References Cited

U.S. PATENT DOCUMENTS 4,880,637 A * 11/1989 Jordan et al.
5,973,191 A    10/1999 Marnett et al.

FOREIGN PATENT DOCUMENTS

| EP | 1 064 940 A1 | 1/2001 |
|---|---|---|
| JP | 04234319 | * 8/1992 |
| WO | WO 98/28292 | 7/1998 |
| WO | WO 98/29382 | 7/1998 |
| WO | WO 99/30721 | 6/1999 |

OTHER PUBLICATIONS

Hardman et al. "Goodman & Gilman's The Pharmacological Basis of Therapeutics" (9th ed, 1996) p. 51.*
Pessoa et al. "Lamivudine Therapy of Chronic Hepatitis B", Ed by Mills et al. 1999, p. 1–10.*
Budavari et al. The Merck Index, (12th ED), 1996, p. 688.*
Kalgutkar et al., Science, (1998), 280(5367), 1268–70.
PCT International Search Report, PCT/NL01/00222, dated Aug. 17, 2001, 2 pages.
PCT International Preliminary Examination Report, PCT/NL01/00222, dated May 14, 2002, 6 pages.

* cited by examiner

*Primary Examiner*—Shaojia Anna Jiang
(74) *Attorney, Agent, or Firm*—TraskBritt

(57) ABSTRACT

The invention relates to the field of antiviral agents, and more specifically to antiviral therapy. The invention provides use of at least one compound or mixture of compounds of the general formula

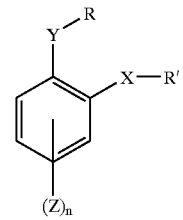

or a functional equivalent or pharmaceutically acceptable salt or hydrate thereof for the production of a pharmaceutical composition for the treatment of a viral infection.

6 Claims, 13 Drawing Sheets

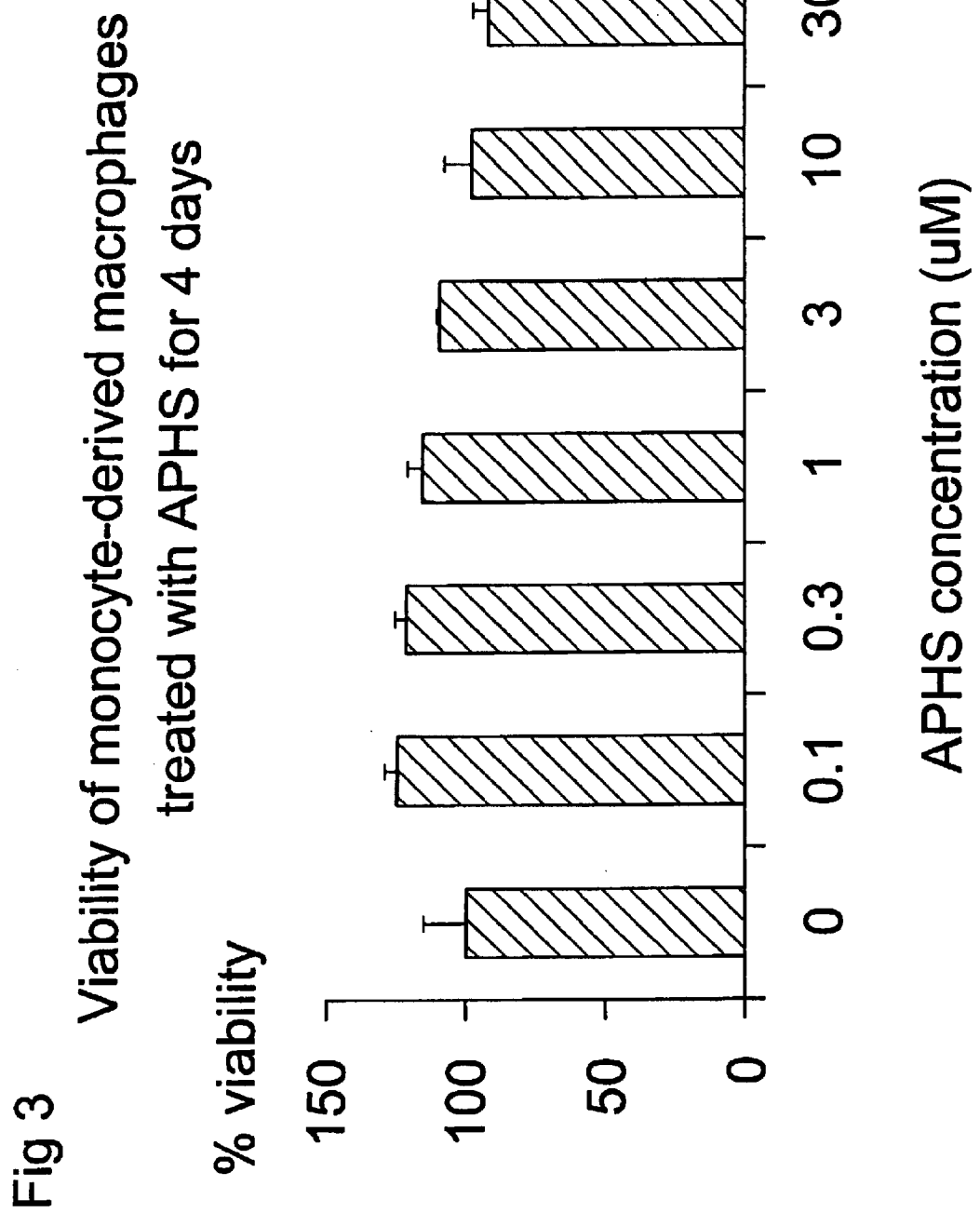

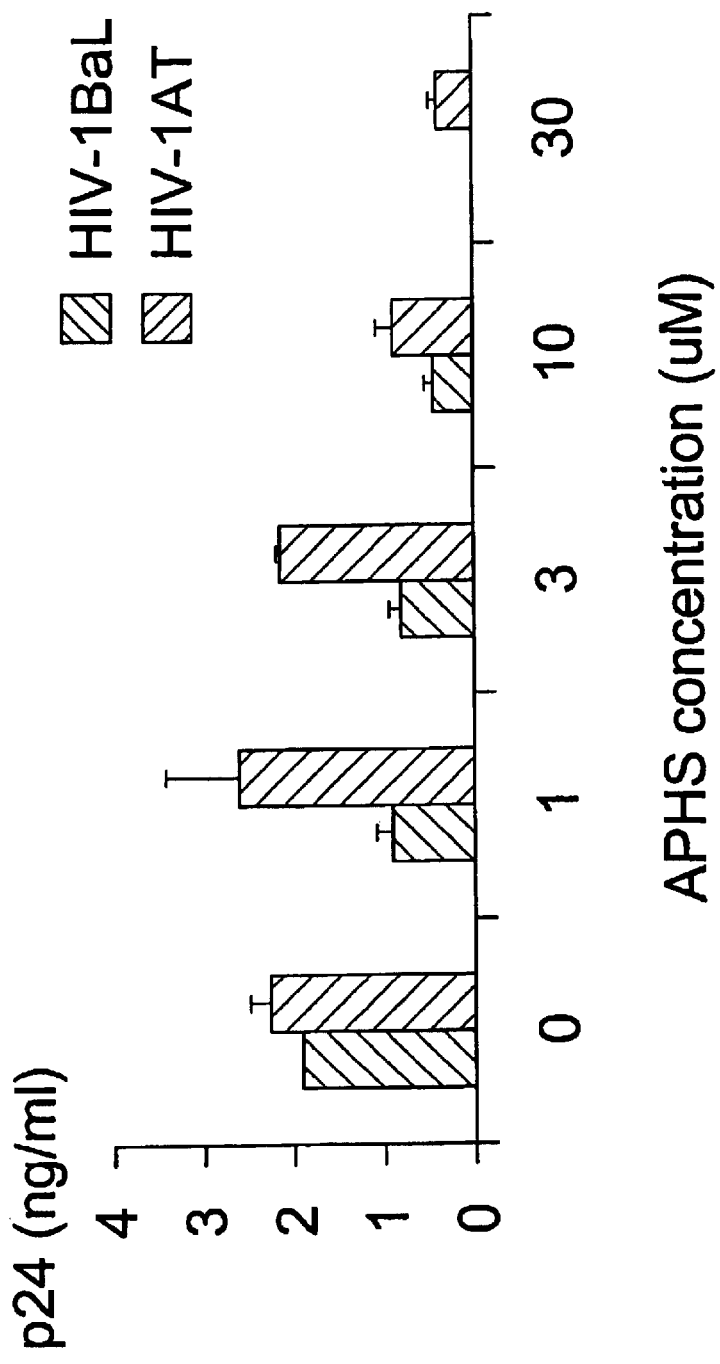

| | X | Y | Z | A | B | D | E | IC$_{50}$ |
|---|---|---|---|---|---|---|---|---|
| APHS | O | S | H | C | O | CH$_3$ | CH$_2$C≡C(CH$_2$)$_3$CH$_3$ | 3.73 |
| LM-3177 | O | SO$_2$ | H | C | O | CH$_3$ | CH$_2$C≡C(CH$_2$)$_3$CH$_3$ | 4.09 |
| LM-3189 | O | S | H | C | O | CH$_3$ | (CH$_2$)$_6$CH$_3$ | 4.92 |
| LM-3142 | O | S | H | H | — | — | CH2C≡C(CH$_2$)$_3$CH$_3$ | 27.46 |
| LM-3155 | O | S | H | C | O | CH$_3$ | CH$_3$ | 222.64 |
| Aspirin | C | C | H | C | O | CH$_3$ | CO$_2$H | 526.51 |

Z  H, SH, $SCH_3$, $SCH_2CH_3$, $SCH(CH_3)_2$, $SC(CH_3)_3$, $S(CH_2)_6CH_3$, $CH_2C\equiv C(CH_2)_3CH_3$ A  -, C, H, $H_2$, $CH_3$, $CH_2CH_3$, $CH_2CH_2CH_3$, $CH_2(CH_2)_2CH_3$, $CH_2(CH_2)_3CH_3$, $CH_2(CH_2)_4CH_3$, $CH_2(CH_2)_5CH_3$, $CH_2(CH_2)_6CH_3$

B  -, O, H, $H_2$, SH, $SCH_3$, $SCH_2CH_3$, $SCH(CH_3)_2$, $SC(CH_3)_3$

D  -, $CH_3$

E  -, $CO_2H$, $CH_3$, $CH_2CH_3$, $CH_2CH_2CH_3$, $CH(CH_3)_2$, $C(CH_3)_3$, $CH_2C\equiv C(CH_2)_3CH_3$, $CH_2(CH_2)_6CH_3$

Fig.11

ANTIVIRAL THERAPY

CROSS-REFERENCE TO RELATED APPLICATIONS

This application is a continuation in part of U.S. Ser. No. 09/608,716 filed on Jun. 30, 2002, now U.S. Pat. No. 6,387,959 which itself claims priority from U.S. Provisional application No. 60/142,297 filed on Jul. 2, 1999.

TECHNICAL FIELD

The invention relates to antiviral agents, and more specifically to antiviral therapy.

BACKGROUND

One of the great paradoxes of modem medicine is that the simplest of organisms can be the most difficult to control. While great progress has been made in controlling more complex organisms such as bacteria, with hundreds of different antibacterial pharmaceutical compositions or antibiotics, there are very few pharmaceutical compositions intended or adapted for antiviral therapy that are of proven effectiveness.

The major drawback in developing antiviral agents has been an inability to distinguish viral replicative mechanisms from host replicative processes. Nevertheless, progress has been made over the past two decades in discovering molecules necessary for virus replication, in characterising them mechanistically, and in developing antiviral agents to inhibit them (see, for review, Hirsch et al., In: *Fields Virology*, Chapter 15, (Lippincot-Raven Publishers, 1996). Well known antiviral agents include amantadine, rimandatine and other anti-influenza agents, acyclovir, gangcyclovir and related agents, foscarnet and other anti-herpes virus agents, ribavirine and various antiretroviral agents as discussed below.

Progress and understanding in the field of antiretroviral therapy in the past few years has been dramatic (see, Hammer and Yeni. AIDS, 12:S181–S188, (1998)). Three major advances have fuelled progress. First, increasing knowledge of disease pathogenesis has provided underpinnings for current therapeutic rationale. The proliferative nature of the viral replicative process ($10^{10}$ virions produced and destroyed each day), the rapid viral turnover (virion plasma half-life of 6 h or less), and the recognition of second and third phases of viral decay under the influence of potent antiretroviral therapy resulting from the presence of longer-lived cell reservoirs has guided the current principles of antiretroviral therapy. The second advance has been the widening array of therapeutic choices represented by the increasing numbers of agents available to patients and clinicians. Third, the availability of increasingly sophisticated patient monitoring techniques, such as viral load determinations, has simultaneously provided the tools for dissecting HIV disease pathogenesis and monitoring the effects of treatment in affected individuals. Taken together, these developments have led to the generally accepted principle that potent combination regimens (also called "highly active antiviral therapy" or "HAART") designed to drive and maintain plasma HIV-RNA concentration below the limits of detection of currently available assays are the treatments of choice.

However, a number of practical limitations to this idealised approach have increasingly been recognised. These include: the variability of initial virologic response according to the disease stage, particularly the high rate of failure in those with advanced HIV infection; the challenge of patient adherence to complex regimens; drug failure and the threat of multidrug resistance; the lack of predictably effective salvage therapies; the emergence of longer-term toxicities to the protease inhibitor class of compounds; and the sharpening division between populations of the world related to cost and access to effective agents.

In several countries, there are 11 agents approved for the treatment of HIV infection and the reasonable expectation is that the total will rise to 15 shortly. These agents are either HIV reverse transcriptase inhibitors of the nucleoside, non-nucleoside, and nucleotide subclasses or members of the HIV-protease inhibitor class. Although the simple calculation of the number of two-, three- and four-drug combinations would suggest that the regimen choices for initial and alternative therapies are vast, in reality they are much more limited as a result of cross-resistance, toxicities, tolerance, drug or food interactions and other practical considerations. Thus, although it is true that the options for initial potent, combination regimens are increasing, when one considers the limitations on subsequent regimens conferred by the initial choice, one realises the restricted options for long-term virologic suppression that currently exist.

In areas where drug access is not a problem, the current recommended standard for initial therapy is a potent in vivo protease inhibitor combined with two nucleoside analogs with the first alternative being a non-nucleoside reverse transcriptase inhibitor in combination with two nucleoside analogs. However, the emergence of drug resistance during treatment and its association with treatment failure have been described with nearly all of the antiretroviral agents in use or in development. Therefore, resistance testing might be thought to logically assist with the choice of alternative treatment in the setting of treatment failure and assist with the choice of initial therapy when primary drug resistance is suspected. However, many questions exist that need to be answered before resistance testing (either genotypic or phenotypic) becomes accepted as a routine clinical tool. In what setting and to what extent this technology will improve decision-making is not clear and drug resistance is only one of a number of reasons for treatment failure. Resistance testing results are most reflective of the selective pressure of the current drug that might emerge quickly on a new regimen. Further, one cannot always deduce the phenotypic susceptibility of a viral strain from its genotype because of assay sensitivity and resistance mutational interactions. Cross-resistance, particularly to protease inhibitors, may also be a dynamic process in which viruses are "primed" by mutations selected on a previous therapy to develop resistance more quickly when exposed to a new member of the same drug class.

Failure of a particular antiretroviral drug regimen may be defined clinically, immunologically or virologically. Increasingly, for individuals on their initial drug combination, a strict definition of failure is being applied, that is, detectable viremia following previous suppression below the detection below the detection limit of the assay being employed. With the advent of plasma HIV-RNA assays with detection limits at the approximate 50 copies/ml range, this has raised the question of whether a confirmed rise above this threshold should trigger a treatment change given the still limited therapeutic armamentarium.

The advances and the limitations of the currently available antiretroviral agents make it clear that new agents and combinations are urgently needed. On the immediate horizon is the promise of widespread availability of four new agents: abacavir (a nucleoside analog reverse transcriptase inhibitor), efavirenz (a non-nucleoside reverse transcriptase inhibitor), adefovir dipivoxil (a nucleotide reverse transcriptase inhibitor), and amprenavir (a protease inhibitor). These agents will carry with them an increasing number of choices for patients and clinicians but are most likely to benefit antiretroviral-naive or minimally drug-experienced individuals only. Their role in "salvage" regimens is currently under investigation but the potential for cross-resistance with the currently approved agents may well limit their effectiveness in this circumstance.

In conclusion, a next wave of drug development is needed that involves new classes of antiviral agents. Other potential anti-viral agents effective against viral targets are needed to broaden the therapeutic possibilities of viral therapy.

DISCLOSURE OF THE INVENTION

The invention provides a method for treating a viral infection with a first antiviral agent, said infection caused by a virus that is at least partly resistant to a second antiviral agent, in a subject suffering therefrom, said method comprising administering to said subject said first antiviral agent, it being a compound of the general formula

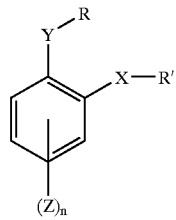

wherein X and Y are independently O, S, SO, $SO_2$, $SO_3$, but preferably O, S, $SO_2$.

"n" is an integer between 0 and 4 inclusive, preferably 1 or 2.

R and R' are independently H with the proviso that when R is H, R' is not H, a $C_1$–$C_{10}$, branched or unbranched, substituted or unsubstituted (preferably the substitute is one or more of halogen or $CF_3$), saturated or (poly)unsaturated, (cyclo)alkyl, alkene, alkyn, (cyclo)aryl, aryl(cyclo)alkyl, (cyclo)alkylaryl, alkoxyaryl, alkoxyalkene, alkoxyalkyne, enyne, diene, diyne or alkoxyalkyl, preferably selected from the group consisting of H, $CH_3$, $CF_3$, $CH_2Cl$, $CH_2Br$, $CH_2CH_3$, $(CH_2)_2CH_3$, $(CH_2)_3CH_3$, $(CH_2)_4CH_3$, $(CH_2)_5 CH_3$, $(CH_2)_6CH_3$, $CH(CH_3)_2$, $CH(CH_3)_3$, $CH=C=CH_2$, $(CH_2)_2O(CH_2)_3CH_3$, $CH_2HC=CH(CH_2)_3CH_3$, $CH_2C\equiv C(CH_2)_3CH_3$, $CH_2C\equiv C(CH_2)_2CH_3$ $CH_2C\equiv CCH_2CH_3$, $CH_2C\equiv CCH_3$ and $CH_2C\equiv CH$ and isomers or homologues thereof; and wherein R' is R, preferably selected from the group consisting of H, $CH_3$,; and wherein R or R' may contain ether linkages or carbonyl or thiocarbonyl functions attached to the ring structure such as ring—(C=O/S)—R/R' and Z is independently R, R', XR, XR', YR or YR' or a functional equivalent, such as a pharmaceutically acceptable salt or hydrate, thereof.

The invention also provides a method for treating a viral infection with a first antiviral agent, said infection caused by a virus that is at least partly resistant to a second antiviral agent, in a subject suffering therefrom, said method comprising administering to said subject said first antiviral agent, it being a compound of the general formula

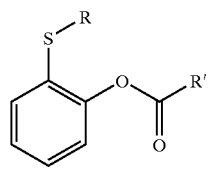

or a functional equivalent, such as a pharmaceutically acceptable salt or hydrate, thereof, in particular wherein R is selected from the group consisting of H, $CH_3$, $CH_2CH_3$, $(CH_2)_2CH_3$, $(CH_2)_3CH_3$, $(CH_2)_4CH_3$, $(CH_2)_5CH_3$, $(CH_2)_6CH_3$, $CH(CH_3)_2$, $CH(CH_3)_3$, $CH=CH=CH_2$, $(CH_2)_2O(CH_2)_3CH_3$, $CH_2HC=CH(CH_2)_3CH_3$, $CH_2C\equiv C(CH_2)_3CH_3$, $CH_2C\equiv C(CH_2)_2CH_3$, $CH_2C\equiv CCH_2CH_3$, $CH_2C\equiv CCH_3$ and $CH_2C\equiv CH$ and isomers or homologues thereof and R' is selected from the group consisting of H, $CH_3$, $CF_3$, $CH_2CL$ and $CH_2Br$.

BRIEF DESCRIPTION OF THE SEVERAL VIEWS OF THE DRAWINGS

FIG. 3—Monocyte-derived macrophages (MDM) were obtained like described in legend of FIG. 2. MDM were then washed twice and cultured for 4 to 7 days in different concentrations of APHS. After a 4 days incubation period cellular viability was assessed by MTT cytotoxicity assay where viable cells convert MTT into a colored formazan dye that can be measured spectrophotometrically. None of the tested concentrations of APHS was found to be cytotoxic.

HIV-1$_{AT}$ at a multiplicity of infection of 0.001, (b) HIV-1$_{BaL}$ at a multiplicity of infection of 0.006 and (c) HIV-1$_{BaL}$ or HIV-1$_{AT}$ at a multiplicity of infection of 0.01 or 0.001, respectively. HIV-infected and mock-infected PBMC were washed twice to remove unbound virus and cultured for 4 to 7 days in different concentrations of APHS. After 4 and 5 days of incubation samples of culture supernatant were collected and p24-core antigen production was quantified using the enzyme-linked immunosorbent assay (ELISA) system of John Moore.

Figure 4A:
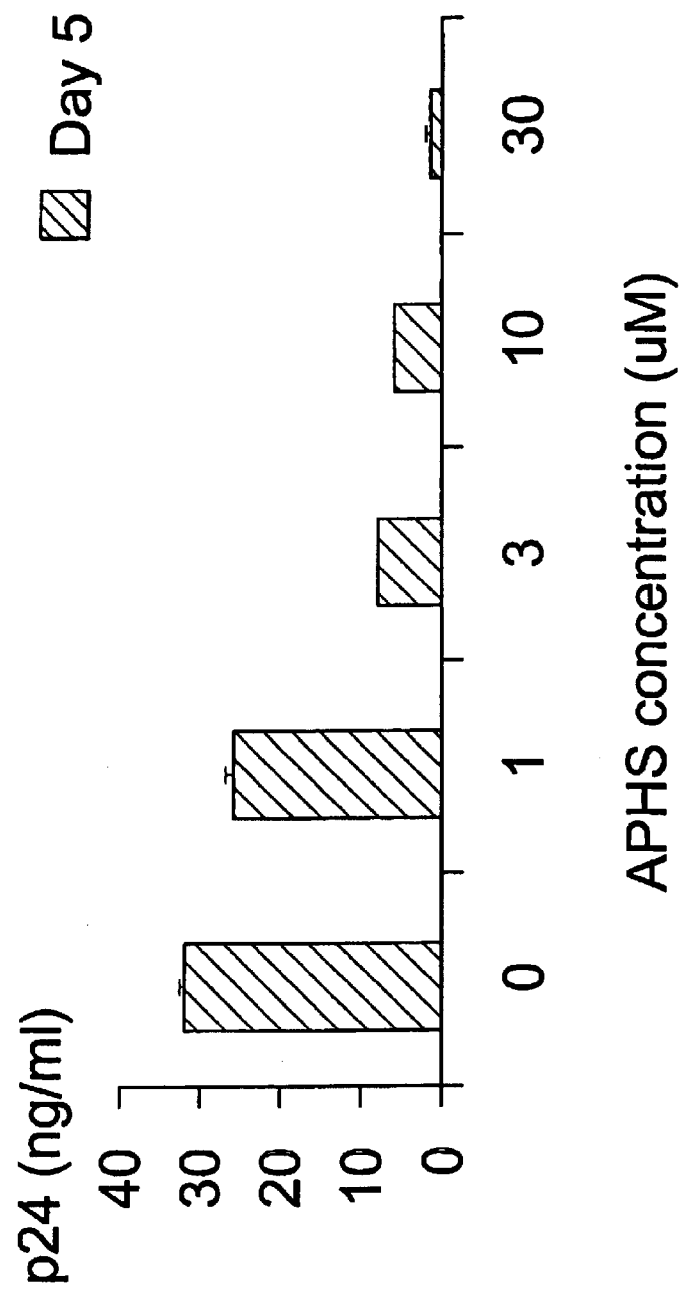
FIG. 4—Peripheral blood mononuclear cells (PBMC) were isolated from heparinized blood from HIV-1-, HIV-2-, and hepatitis B-seronegative donors and obtained on Ficoll-Hypaque density gradients. Cells were washed twice, stimulated with 5 mg/ml phytohemagglutinin (PHA), and cultured in RPMI-1640 medium supplemented with 5 mM Hepes, 19 mM sodium bicarbonate, 10 mg/mL gentamycin, and 10% heat-inactivated fetal calf serum at a concentration of $2\times10^6$ cells/ml. After 3 days of incubation stimulated PBMC were recovered from the flasks and infected for 2 hours with (a)

Concentrations above 1 $\mu$M APHS inhibit HIV-1 production. 30 $\mu$M APHS inhibit HIV-1BaL replication by 100%. When infectivity is lower (FIG. 4c), 1 $\mu$M APHS inhibit HIV-1$_{BaL}$ production by at 50%.

Figure 4B:
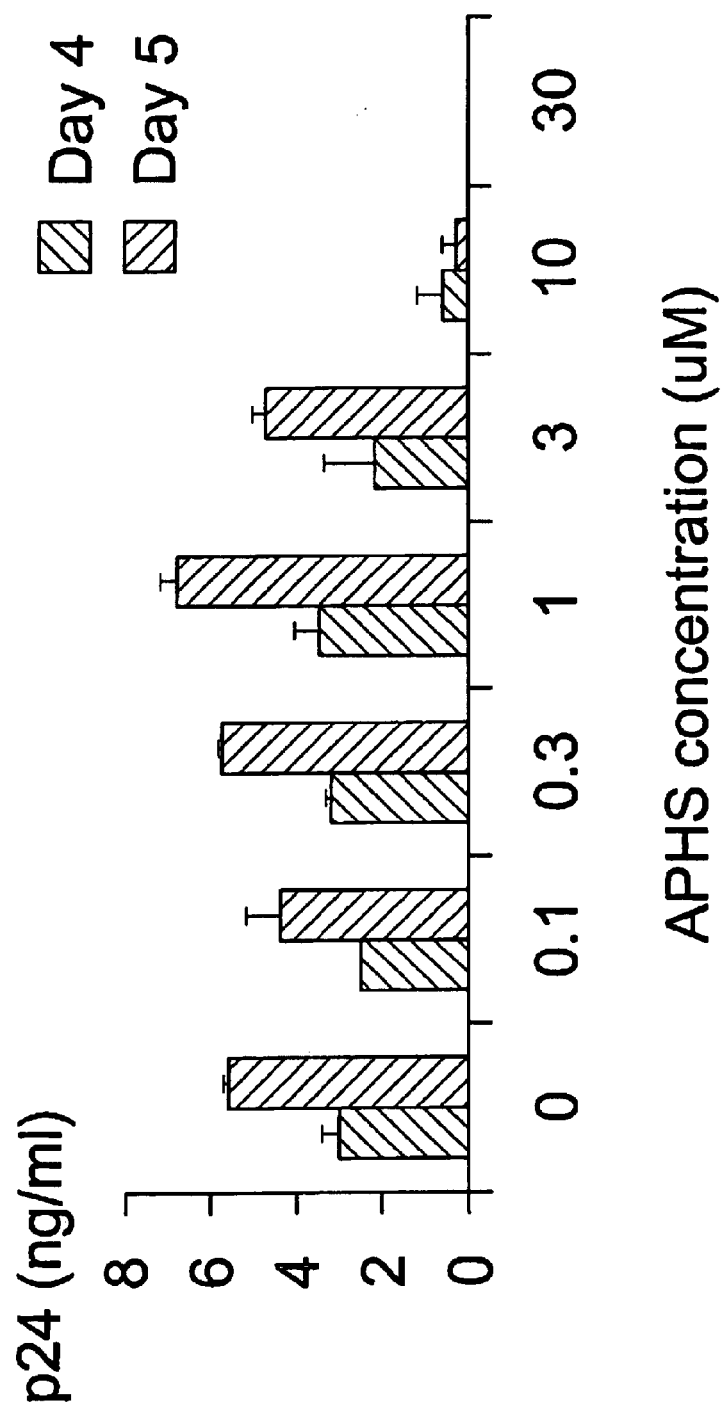
Figure 5:
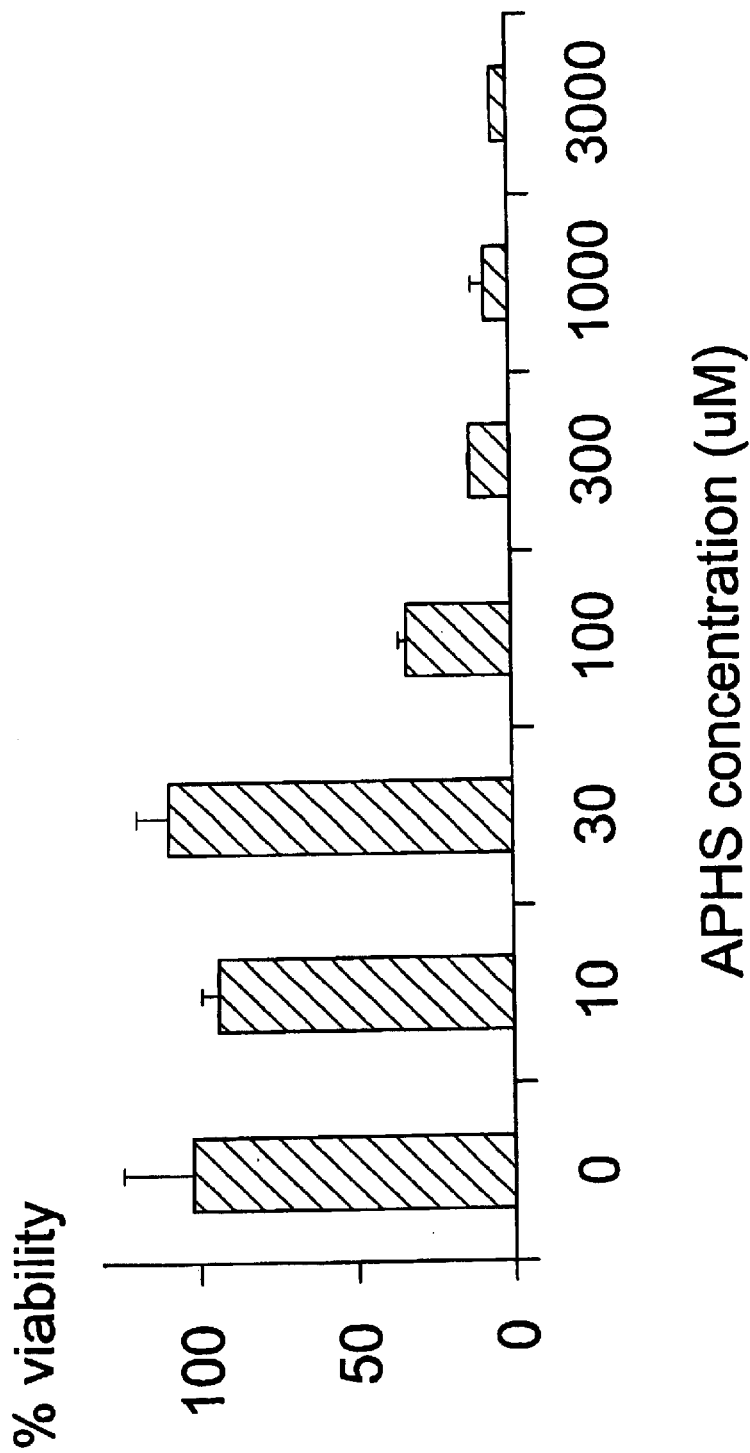

FIG. 5—PBMC were obtained and stimulated as described in legend of FIG. 4. 3 days after incubation PBMC were recovered from the flasks, washed and cultured for 4 to 7 days in different concentrations of APHS. After a 5 days incubation period, cellular viability was assessed by WST-1 cytotoxicity assay where viable cells convert WST-1 into a coloured formazan dye that can be measured spectrophotometrically. Concentrations at or above 100 $\mu$M were found to reduce viability.

Figure 6:
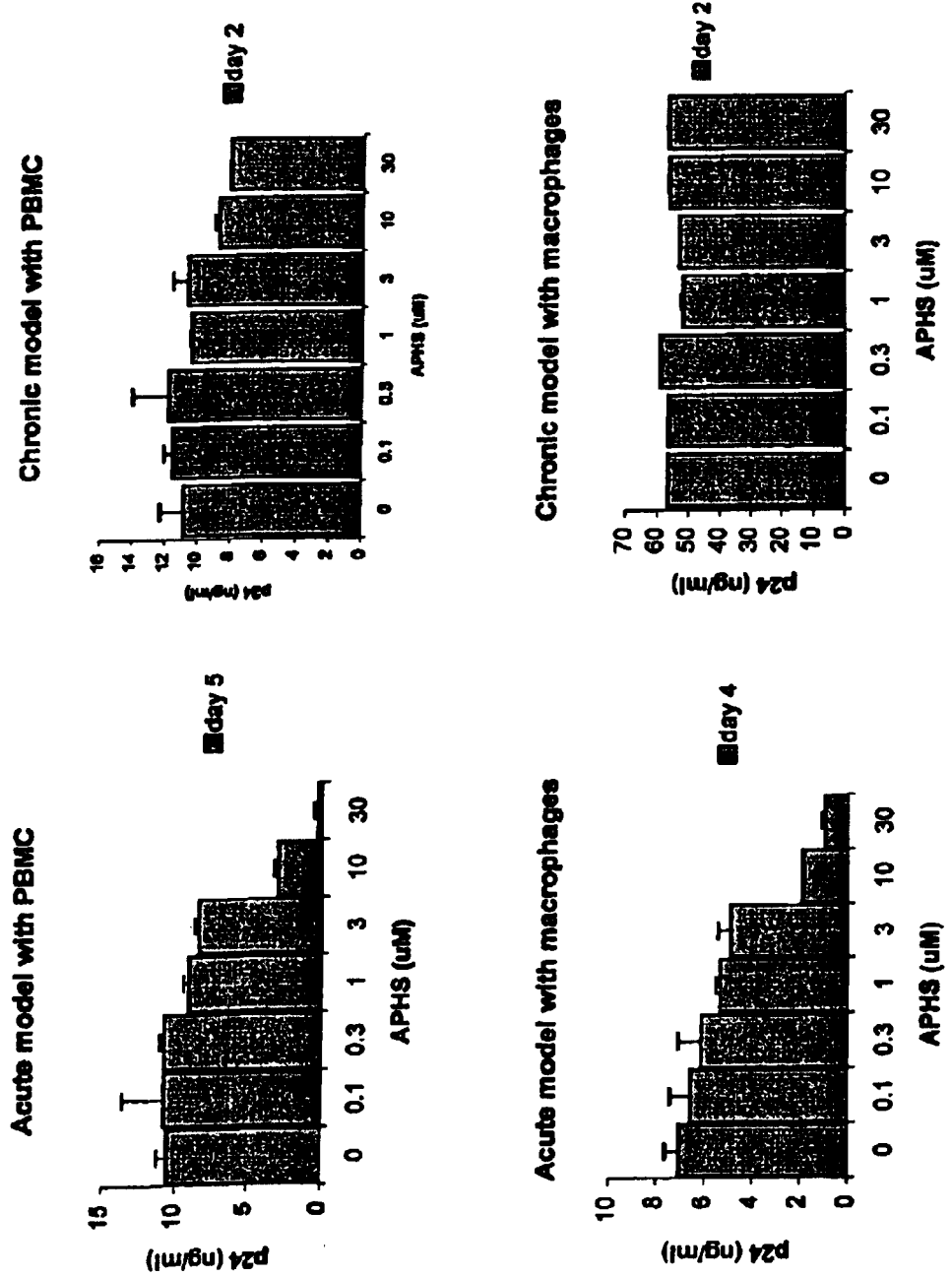

FIG. 6—Effect of APHS on HIV-1$_{Ba-L}$ replication in PBMC (A,B) or MDM (C,D) in an acute (A,C) or chronic (B,D) Model of HIV-1 infection.

Figure 7:
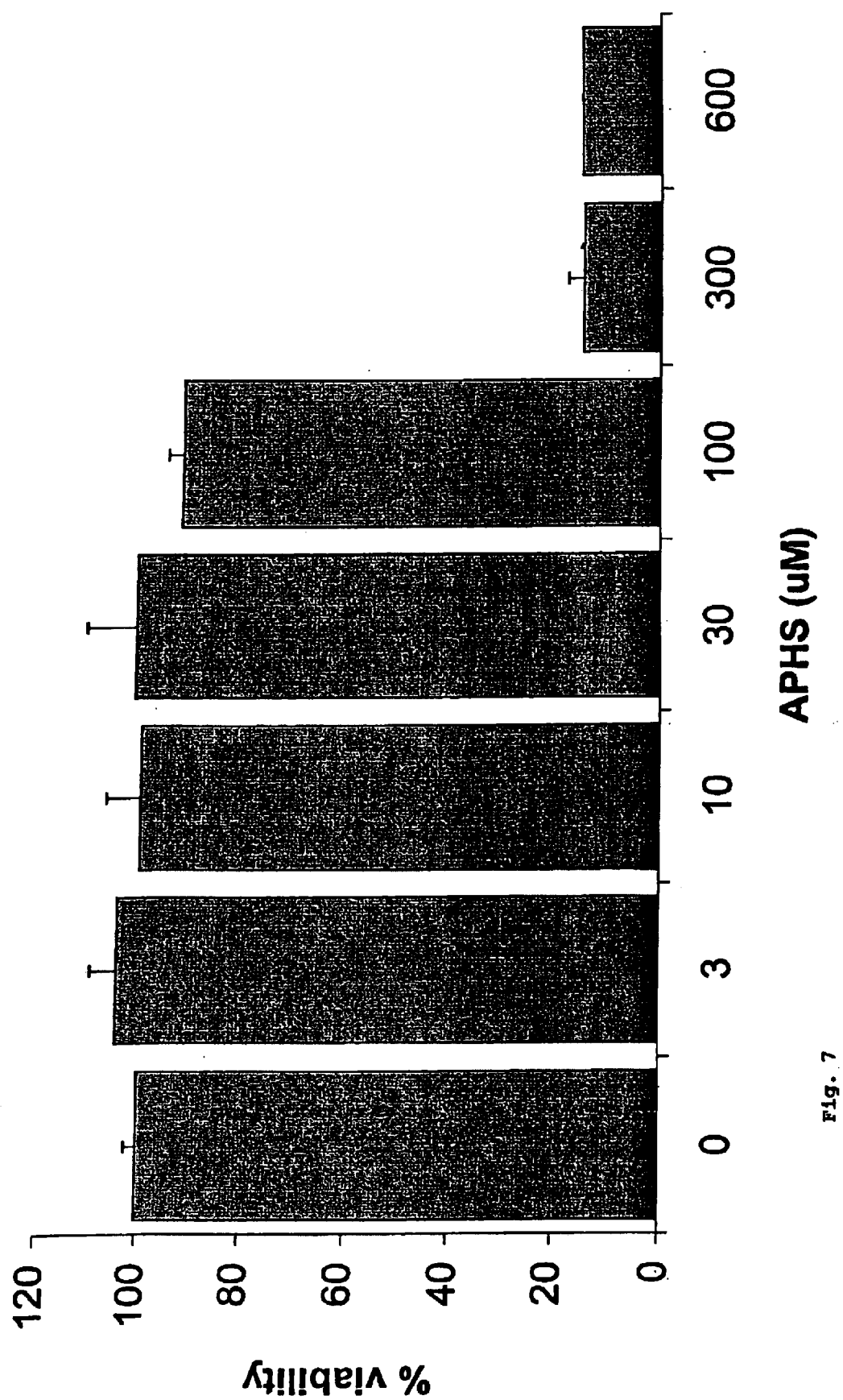

FIG. 7—Viability of monocyte-derived macrophage after APHS treatment.

Figure 8:
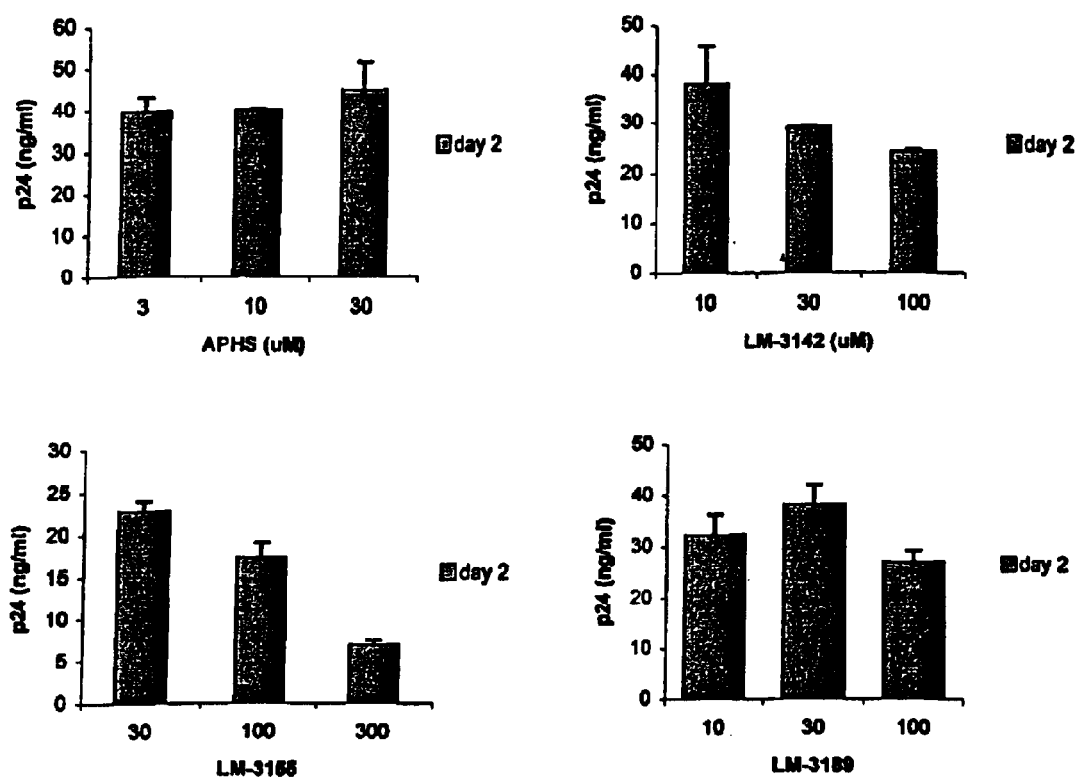

FIG. 8—Effect of APHS on HIV-1 production by U1 cells.

Figure 9:
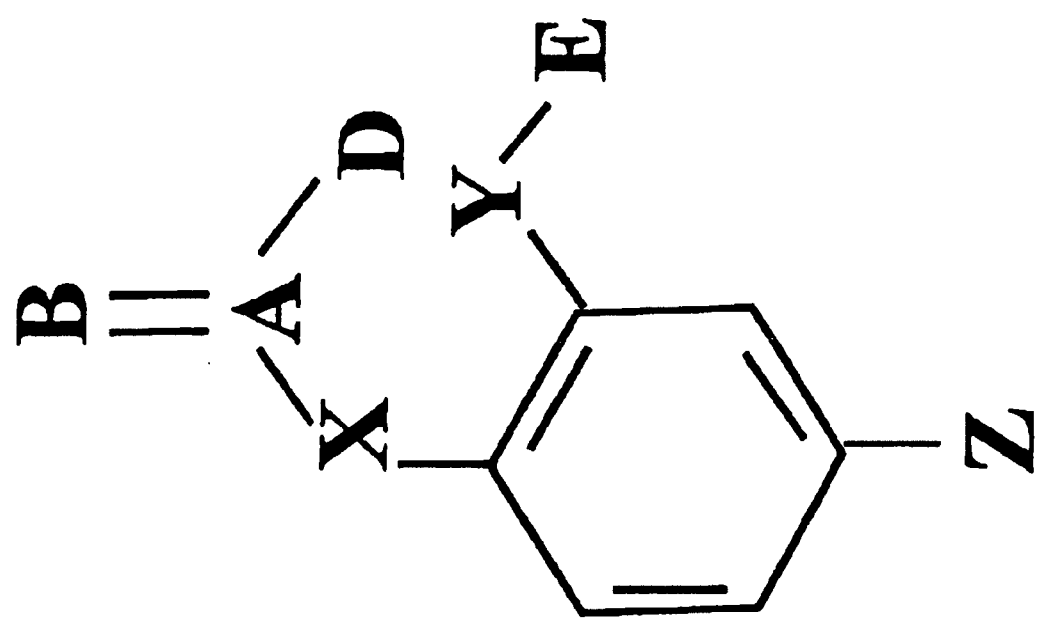

FIG. 9—Structure of a compound described herein.

FIG. 10—The 50% inhibitory concentration (IC$_{50}$) of the compounds APHS, LM-3177, LM-3189, LM-3142, LM-3155 and aspirin that suppresses HIV-1 replication in primary human peripheral blood mononuclear cells. The infection was performed as described herein. The IC50 values are depicted in micromolars. The letters X, Y, Z, A, B, D, E in the first row (upper line) refer to the same letters in the general formula of the compound in FIG. 9.

FIG. 11—Selected chemical structures for letters X, Y, Z, A, B, D, E in the general formula of the compound in FIG. 9. Of particular interest are the combinations in these letters wherein Z=H, Y=S, E=CH$_2$C≡C(CH$_2$)$_3$CH$_3$, X=O, B=-, D=-, and A is either CH$_3$, CH$_2$CH$_3$, CH$_2$CH$_2$CH$_3$, CH$_2$(CH$_2$)$_2$CH$_3$, CH$_2$(CH$_2$)$_3$CH$_3$, CH$_2$(CH$_2$)$_4$CH$_3$, CH$_2$(CH$_2$)$_5$CH$_3$, or CH$_2$(CH$_2$)$_6$CH$_3$ and the combinations in letters wherein Z=H, Y=S, E=C(CH$_3$)$_3$, X=O, A=C, B=O, and D=CH$_3$ and the combinations wherein Z=H, Y=S, E=C(CH$_3$)$_3$, X=-, A=C, B=O, and D=CH$_3$ and the combinations wherein Z=SC(CH$_3$)$_3$, Y=-, E=-, X=O, A=C, B=O, and D=CH$_3$ and the combinations wherein Z=SC(CH$_3$)$_3$, Y=-, E=-, X=-, A=C, B=O, and D=CH$_3$ and the combinations wherein Y=-, E=-, Z=SCH$_2$C≡C(CH$_2$)$_3$CH$_3$, X=O, B=-, D=-, and A is either CH$_3$, CH$_2$CH$_3$, CH$_2$CH$_2$CH$_3$, CH$_2$(CH$_2$)$_2$CH$_3$, CH$_2$(CH$_2$)$_3$CH$_3$, CH$_2$(CH$_2$)$_4$CH$_3$, CH$_2$(CH$_2$)$_5$CH$_3$, or CH$_2$(CH$_2$)$_6$CH$_3$.

BEST MODE OF THE INVENTION

In a preferred embodiment, the invention provides a method wherein the viral infection comprises a retroviral infection.

Advantageously, the method as herein provided is useful when the infection is caused by a virus at least partly resistant to treatment with another antiviral agent, such as one selected from the group of amantadine, rimandatine, acyclovir, gangcyclovir, foscarnet and ribavirine, or as one selected from the group of reverse transcriptase inhibitors or protease inhibitors. Whether the virus present in the diseased or affected subject has acquired or is provided with such resistance can readily be determined with various methods for resistance testing known in the art. Such methods include, for example, obtaining a sample from the subject containing the virus and testing it in cell-culture for its relative susceptibility to the other viral agent, especially in comparison with control viruses of known susceptibilities, or can be deduced from the clinical and/or virological response of the subject to treatment with the other antiviral agent. When a possible treatment of the viral infection with the other antiviral agent is already of proven ineffectiveness because the virus in question is already known to be at least partly resistant against treatment with the other agent, such resistance testing is, at least in the particular case of the diseased subject in question, not necessary.

The invention also provides a compound or pharmaceutical composition for the treatment of a viral infection comprising a compound of a formula as identified herein or a pharmaceutically acceptable salt or hydrate thereof, and a pharmaceutical composition according to the invention that is combined with a pharmaceutical composition that at least comprises another antiviral agent.

The invention also provides a compound, and use thereof, of the general formula

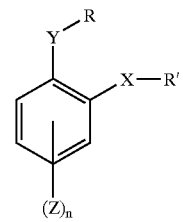

wherein X and Y are independently selected from the group O, S, SO, SO$_2$, and SO$_3$, but are preferably O, S, or SO$_2$. "n" is an integer between 0 and 4, preferably 1 or 2.

R and R' are independently H, a C$_1$–C$_{10}$, branched or unbranched, substituted or unsubstituted (preferably the substitute is one or more of halogen or CF$_3$), saturated or (poly)unsaturated, (cyclo)alkyl, alkene, alkyn, (cyclo)aryl, aryl(cyclo)alkyl, (cyclo)alkylaryl, alkoxyaryl, alkoxyalkene, alkoxyalkyne, enyne, diene, diyne or alkoxyalkyl (with the proviso that when R is H, R' is not H), preferably selected from the group consisting of H, CH$_3$, CF$_3$, CH$_2$CL, CH$_2$Br, CH$_2$CH$_3$, (CH$_2$)$_2$CH$_3$, (CH$_2$)$_3$CH$_3$, (CH$_2$)$_4$CH$_3$, (CH$_2$)$_5$CH$_3$, (CH$_2$)$_6$CH$_3$, CH(CH$_3$)$_2$, CH(CH$_3$)$_3$, CH=C=CH$_2$, (CH$_2$)$_2$O(CH$_2$)$_3$CH$_3$, CH$_2$HC=CH(CH$_2$)$_3$CH$_3$, CH$_2$C≡C(CH$_2$)$_3$CH$_3$, CH$_2$C≡C(CH$_2$)$_2$CH$_3$, CH$_2$C≡CCH$_2$CH$_3$, CH$_2$C≡CCH$_3$ and CH$_2$C≡CH and isomers or homologues thereof, wherein R' is R, preferably selected from the group consisting of H, CH$_3$; and wherein R or R' may contain ether linkages or carbonyl or thiocarbonyl functions attached to the ring structure such as ring—(C═O/S)—R/R', and Z is independently R, R', XR, XR', YR or YR' or a functional equivalent thereof for the production of a pharmaceutical composition for the treatment of a viral infection.

The present invention also provides (use of) at least one compound or mixture of compounds of the general formula

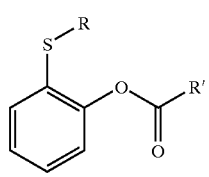

or a functional equivalent or pharmaceutically acceptable salt or hydrate thereof for the production of a pharmaceutical composition for the treatment of a viral infection. Replacements or substitutions of the general formula for example comprise replacing S with O, Se or Te, and/or additionally substituting the ring with one or more side groups such as R or R'. Functional equivalent compounds, as regard to antiviral activity (shown as tested) are for example found among those of FIG. 9. Preferred are the combinations as indicated in FIG. 11 wherein Z is H, Y is S, E is $CH_2C\equiv C(CH_2)_3CH_3$, X is O, B=-, D=-, and A is either $CH_3$, $CH_2CH_3$, $CH_2CH_2CH_3$, $CH_2(CH_2)_2CH_3$, $CH_2(CH_2)_3CH_3$, $CH_2(CH_2)_4CH_3$, $CH_2(CH_2)_5CH_3$, or $CH_2(CH_2)_6CH_3$ and the combinations in letters wherein Z=H, Y=S, E=$C(CH_3)_3$, X=O, A=C, B=O, and D=$CH_3$ and the combinations wherein Z=H, Y=S, E=$C(CH_3)_3$, X=-, A=C, B=O, and D=$CH_3$ and the combinations wherein Z=$SC(CH_3)_3$, Y=-, E=-, X=O, A=C, B=O, and D=$CH_3$ and the combinations wherein Z=$SC(CH_3)_3$, Y=-, E=-, X=-, A=C, B=O, and D=$CH_3$ and the combinations wherein Y=-, E=-, Z=$SCH_2C\equiv C(CH_2)_3$ $CH_3$, X=O, B=-, D=-, and A is either $CH_3$, $CH_2CH_3$, $CH_2CH_2CH_3$, $CH_2(CH_2)_2CH_3$, $CH_2(CH_2)_3CH_3$, $CH_2(CH_2)_4CH_3$, $CH_2(CH_2)_5CH_3$, or $CH_2(CH_2)_6CH_3$.

Also, the results of compounds of FIG. 9, shown in FIG. 10, shows a benzene ring comprising an ester, an ether or a hydroxyl group and comprising a lipophilic side chain being involved in anti-viral activity. Furthermore, LM-3155 is about 100-fold less efficient in inhibiting viral replication showing that the size of Y-R in the general formula or functionally equivalent compound as provided by the invention generally should be long. By reducing the size of Y-R in the general formula the compound becomes more hydrophilic. Thus, Y-R should be long in order to increase the lipophilic properties of the compound and therefore the anti-viral activity. An alternative is to keep the size of Y-R short and to add long groups at place Z in the general formula of the compound. In addition, although the anti-viral activity of LM-3142 is about 10-fold lower this finding suggests that the ester group is not absolutely necessary for its anti-viral activity. The reason that LM-3142 has a lower anti-viral activity is likely due to its decreased lipophilicity. Increasing its lipophilicity otherwise will again increase its anti-viral activity. Furthermore, because of the acetylester of APHS the compound hydrolyzes quickly and therefore the lipophilicity is reduced. Therefore, alternatives are provided wherein the acetylester is replaced by less easily hydrolysing side groups such as by an ethylether, propylether, butylether, pentylether, hexylether, or heptylether. The half-lives of these functionally equivalent compounds is much longer and therefore a better anti-viral activity is provided.

A particularly useful compound is identified in Table 3, especially the compound identified as c2, c3, c5 or c7, or a derivative thereof. Side group D (see, FIG. 9) is preferably substituted with an electron withdrawal group. Useful are groups such as $CF_3$, $NO_2$ or CN.

Compounds of the general formula are for example known from Arnoldi et al., *J. Chem. Soc.*, Perkin Trans. 1 (1993), 12:1359-1366; from Poirier et al., *Sulfur Lett.* (1998) 10:167-173; and from Ohtsuka et al., *Chem. Pharm. Bull.* (1983) 31:443-453. Furthermore, it is known from Kalgutar et al., *Science* 280:1268-1270, (1998) and PCT International Patent Publication WO 98/29382 that several compounds of the general formula covalently inactivate cyclo-oxygenase-2 ("COX-2") and are selective inhibitors of prostaglandin endoperoxidase-2 and that a pharmaceutical composition comprising such compound may be useful for providing pain-relief, such as in the prophylaxis or therapeutic treatment of inflammatory responses such as oedema, fever, analgesia, neuromuscular pain, headache, cancer pain or arthritic pain.

Surprisingly, however, it is now found that a pharmaceutical composition comprising the compound is useful in anti-viral therapy. It is not necessary to maintain the COX-2 inhibiting activity of the agent to maintain its antiviral activity. Not wishing to being bound by theory it is herein assumed that a compound of the general formula or a functional equivalent thereof antagonises activities of transcription factors such as AP-1, STAT and NF-κB, presumably with the effect that viral functions such as virus transcription and/or viral gene expression are functionally inhibited, as, for example, can be detected by testing the effect of such compound on viral promoter activity (see, e.g., FIG. 1). Alternatively, the effect on viral protein expression is detected by testing viral protein production in cell culture (see, e.g., FIGS. 2, 4a and 4b).

A preferred embodiment of the invention involves the use of a compound of the general formula as above or a pharmaceutically acceptable salt or hydrate thereof wherein R is H, $CF_3$ or a C1–C10 (but due to its increase lipophilicity preferably a C4–C10, branched or unbranched, substituted or unsubstituted (preferably the substitute is a halogen), saturated or (poly)unsaturated, (cyclo)alkyl, alkene, alkyn, (cyclo)aryl, aryl(cyclo)alkyl, (cyclo)alkylaryl, alkoxyaryl, alkoxyalkene, alkoxyalkyne, enyne, diene, diyne or alkoxyalkyl, preferably selected from the group consisting of H, $CH_3$, $CH_2CH_3$, $(CH_2)_2CH_3$, $(CH_2)_3CH_3$, $(CH_2)_4CH_3$, $(CH_2)_5CH_3$, $(CH_2)_6CH_3$, $CH(CH_3)_2$, $CH(CH_3)_3$, $CH=C=CH_2$, $(CH_2)_2O(CH_2)_3CH_3$, $CH_2HC=CH(CH_2)_3$ $CH_3$, $CH_2C\equiv C(CH_2)_3CH_3$, $CH_2C\equiv C(CH_2)_2CH_3$, $CH_2C\equiv CCH_2CH_3$, $CH_2C\equiv C$ $CH_3$ and $CH_2C\equiv CH$ and isomers or homologues thereof; and wherein R' is R, preferably selected from the group consisting of H, $CH_3$, $CF_3$, $CH_2CL$ and $CH_2Br$.

The present invention also provides a pharmaceutical composition intended and adapted for the treatment of a viral infection (herein also called an antiviral agent) comprising at least one compound or a mixture of compounds according to the general formula and a pharmaceutically acceptable carrier of diluent. In order to use a compound according to the general formula or a pharmaceutically acceptable salt or hydrate thereof in therapy, it will normally be formulated into a pharmaceutical composition in accordance with standard pharmaceutical practice. This invention, therefore, also relates to a pharmaceutical composition for the treatment of a viral infection comprising an effective amount of a compound according to the general formula, or a pharmaceutically acceptable salt or hydrate thereof, and pharmaceutically acceptable carrier or diluent. A pharmaceutical composition as provided by the invention allows treatment in a conveniently wide therapeutic window, toxicity for cells, as for example evaluated on the level of cell-viability as shown in FIGS. 3 and 5, is not or only little detected in ranges (see, FIGS. 2, 4a and 4b) where significant anti-viral activity is found.

In a preferred embodiment, the invention provides a use according to the invention wherein the viral infection is caused by a virus at least partly resistant against treatment with another antiviral agent such as for example shown in the detailed description wherein the use is provided with an infection that is caused by a retrovirus at least partly resistant against treatment with another antiviral agent such as a reverse transcriptase inhibitor or protease inhibitor.

In a preferred embodiment, the invention provides use according to the invention wherein the viral infection comprises a retroviral infection. Such a retroviral infection can, for example, comprise a leukaemia virus infection, such as caused by bovine leukaemia virus or human T-cell-leukaemia virus. Other retroviral infections known in the art are for example ovine lentivirus infections or spumaretrovirus infections. Also, such a retroviral infection can comprise an infection with a recombinant retrovirus that is, for example, constructed for use in gene therapy. Preferably, the invention provides use according to the invention wherein the retroviral infection is caused by an immunodeficiency virus such as human or simian immunodeficiency virus (HIV or SIV). As an example, HIV-1 infection of T-cells and macrophages is mediated by CD4 and the recently discovered chemokine receptors such as CCR-5, CXCR-4, CCR2b and CCR-3. After binding of HIV-1 gp120 to these receptors fusion of viral and cellular membranes occurs resulting in the release of the viral pre-integration complex into the cytoplasm. Subsequently the matrix domain of the HIV-1 gag protein mediates the translocation of the HIV-1 pre-integration complex to the nucleus. Formation of HIV-1 DNA occurs already within the pre-integration complex and can even be formed within the intact virion itself. Complete HIV-1 DNA consists in several forms but, however, a crucial step in infection is the integration of viral DNA into the chromosomal host cell DNA. At this stage in the viral life cycle the cell is infected for life. Current anti-HIV compounds are directed against various stages in the HIV-1 life cycle. For instance, the nucleoside and non-nucleoside analogs are directed against reverse transcriptase, the enzyme that converts the viral RNA into DNA. In such a way virions released by HIV-infected cells are not infectious for other target cells, unless mutations in the reverse transcriptase occur that confer resistance to these classes of anti-HIV drugs. Another class of anti-HIV compounds that is part of all new triple anti-HIV therapy treatment regimens are the protease inhibitors. These compounds likely prevent the formation of complete virions by HIV-infected cells and thus are intended to prevent the spread of HIV-1 to new target cells. Herein is for example shown in FIGS. 2, 4a and 4b that a pharmaceutical composition comprising a compound according to the general formula as provided by the invention provides anti-HIV activity as well, allowing for a novel antiviral therapy provided by the invention.

The invention furthermore provides use according to the invention wherein the treatment additionally comprises treatment with another pharmaceutical composition. For example, combinatorial therapy to treat virus infections, as is often the case when HIV-infected individuals are treated is now provided wherein the other pharmaceutical composition at least comprises an antiviral agent, such as for example amantadine and rimandatine or another anti-influenza agents, acyclovir, gangcyclovir or related agent, foscarnet or other anti-herpes virus agent, ribavirine or a antiretroviral agent, or an antiviral agent as provided by the invention. Of course, combination therapies including an anti-viral agent according to the invention, and additionally comprising more than one additional anti-viral agent, such as combinations of the anti-viral agent as provided by the invention with nucleoside analogue reverse transcriptase inhibitors and/or with non-nucleoside reverse transcriptase inhibitors and/or with nucleotide analogue reverse transcriptase inhibitors and/or with protease inhibitors is provided as well, also since an anti-viral agent as provided by the invention is particularly effective against otherwise drug-resistant viruses.

Additionally, the invention provides use according to the invention wherein the treatment additionally comprises treatment of inflammatory responses, such as such as oedema, fever, pain, neuromuscular pain, headache, cancer or arthritic pain, viral-infection-related or -associated dementias, or other bodily ailments.

Furthermore, the invention provides a pharmaceutical composition intended and adapted for anti-viral therapy comprising a compound of the general formula or functional equivalent thereof. Preferably, the pharmaceutical composition intended and adapted for anti-viral therapy comprises a compound of the general formula wherein R or R' are as defined above. Preferably, an anti-viral agent as provided by the invention comprises 2 acetoxythioanisole, 2-(trifluoromethylacetoxy)thioanisole, 2-($\alpha$-chloroace-toxy)thioanisole, 2-($\alpha$-bromoacetoxy)thioanisole, 2-acetoxyphenylbenzyl sulfide, 2-acetoxyphenzyl-2-phenylethyl sulfide, 2-acetoxyphenylethyl sulfide, 2-acetoxyphenylpropyl sulfide, 2-acetoxyphenyl-butyl sulfide, 2-acetoxyphenylpentyl sulfide, 2-acetoxyphenylhexyl sulfide, 2-acetoxyphenylheptyl sulfide, 2-acetoxyphenyl-2-butoxyethyl sulfide, 2-acetoxyphenyl-2-trans-heptenyl sulfide, 2-acetoxyphenylhept-2-ynyl sulfide, 2-acetoxyphenylbut-2-ynyl sulfide, 2-acetoxyphenylprop-2-ynyl sulfide, or o-(acetoxy-phenyl)hept-2-ynyl sulfide (APHS), or a pharmaceutically acceptable salt or hydrate thereof. Suitable pharmaceutically acceptable salts are well known to those skilled in the art and include basic salts of inorganic and organic acids, such as hydrochloric acid, hydrobromic acid, sulfonic acid, phosphoric acid, methane sulfonic acid, ethane sulfonic acid, acetic acid, malic acid, tartaric acid, maleic acid, benzoic acid, salicylic acid, phenylacetic acid and mandelic acid. In addition, pharmaceutically acceptable salts of a compound according to the general formula may also be formed with a pharmaceutically acceptable cation, for instance, if a substituent group comprises a carboxy moiety. Suitable pharmaceutically acceptable cations are well known in the art and include alkaline, alkaline earth ammonium and quaternary ammonium cations.

In addition, the invention provides a pharmaceutical composition intended and adapted for anti-viral therapy comprising a compound of the general formula or functional equivalent thereof the composition at least combined, preferably mixed with a pharmaceutical composition that at least comprises another antiviral agent, such as for example amantadine and rimandatine or another anti-influenza agents, acyclovir, gangcyclovir or related agent, foscarnet or other anti-herpes virus agent, ribavirine or a antiretroviral agent, or an antiviral agent as provided by the invention. Such a composition as provided by the invention can advantageously be used in combinatorial anti-viral therapy.

The invention also provides a method to treat a viral infection of an animal comprising administering to the animal an anti-viral agent according to the invention or subjecting the animal to treatment with an anti-viral agent according the invention. An anti-viral agent comprising a compound according to the general formula, a pharmaceutically acceptable salt thereof and a pharmaceutical composition incorporating such, may be conveniently administered by any of the routes conventionally used for drug administration, for example, orally, topically, parenterally, or by inhalation. A compound according to the general formula may be administered in conventional dosage forms prepared by combining a compound according to the general formula with a standard pharmaceutical carrier according to conventional procedures.

An anti-viral agent comprising a compound according to the general formula may be administered parenterally, for example, by intravenous, intramuscular, subcutaneous, intranasal, intrarectal, intravaginal or intraperitoneal administration. Subcutaneous and intramuscular forms of parenteral administration are generally preferred. Appropriate dosage forms and dosage regimes for such administration may be prepared by conventional techniques or arrived at by dose finding studies. Compounds may also be administered by inhalation e.g., intranasal and oral inhalation administration. Appropriate dosage forms or regimes for such administration, such as aerosol formulation or metered dose inhaler may be prepared by conventional techniques well known to those having ordinary skill in this art.

An anti-viral agent of the present invention may also be administered in combination with a known, second therapeutically active compound or composition. These procedures may involve mixing, granulating and compressing or dissolving the ingredients as appropriate to the desired preparation. It will be appreciated that the form and character of the pharmaceutically acceptable carrier or diluent is dictated by the amount of active ingredient with which it is to be combined, the route of administration and other well known variable. The carrier(s) must be "acceptable" in the sense of being compatible with the other ingredients of the formulation and not deleterious to the recipient thereof.

In particular, the invention provides a method to treat a viral infection comprising administering to the animal an anti-viral agent according to the invention or subjecting the animal to treatment with the agent wherein the viral infection is a retroviral infection. In particular, the invention provides a method to treat a viral infection wherein the animal is human. In the case of viral infections it is considered especially advantageous to combine treatment of a viral infection with an anti-viral agent according to the invention with treatment with at least one other anti-viral agent, thereby greatly enhancing the possible number of combinations that can be used to for example treat patients with retroviral infections such as AIDS or AIDS-related infections, thereby enhancing therapeutic possibilities for combinatorial or highly active antiviral therapy (HAART), especially under those circumstances wherein viral isolates may emerge or are already present in the patient that are otherwise at least partly resistant to other viral drugs such as a reverse transcriptase inhibitor or protease inhibitor.

The invention is further explained by use of the following illustrative Examples.

EXAMPLES

Material and Methods
1. Materials and Methods Related to Cells
1.a. Isolation and Culture of Peripheral Blood Mononuclear Cells Peripheral blood mononuclear cell (PBMC) fractions are isolated from heparinised blood from HIV-1-, HIV-2- and hepatitis B-seronegative donors (Blood-bank, Utrecht, the Netherlands) by Ficoll-Isopaque gradient separation. Cells are washed twice, stimulated with 4 µg/ml phytohemagglutinin (PHA), and cultured in RPMI-1640 medium supplemented with 5 mM Hepes, 19 mM sodium bicarbonate, 10 µg/ml gentamycin, and 10% heat-inactivated fetal calf serum at a concentration of $1 \times 10^6$ cells/ml.

1.b. Isolation and Culture of Monocyte-Derived Macrophages (MDM)

PBMC are isolated from heparinized blood from HIV-1-, HIV-2-, and hepatitis B-seronegative donors and obtained on Ficoll-Hypaque density gradients. Cells are washed twice and monocytes are purified by countercurrent centrifugal elutriation. Cells are >98% monocytes by criteria of cell morphology on May-Grünwald-Giemsa-stained cytosmears and by nonspecific esterase staining using alpha-naphtylacetate (Sigma Chemical Co., St. Louis, Mo.) as substrate. Monocytes are cultured in suspension at a concentration of $2 \times 10^6$ cells/ml in Teflon flasks (Nalgene, Rochester, N.Y.) in Iscove's modified Dulbeco's medium (IMDM) with 10% heat-inactivated human AB serum negative for anti-HIV antibodies, 10 mg/ml gentamycin, and 10 mg/ml ciprofloxacin (Sigma) for 7 days.

1.c. Peripheral Blood Lymphocyte Isolation

PBMC fractions are isolated from heparinized blood from HIV-1-, HIV-2- and hepatitis B-seronegative donors (Blood-bank, Utrecht, the Netherlands) by Ficoll-Isopaque gradient separation. After the cells are washed twice monocytes are allowed to adhere on fibronectin-coated flasks before the PBL fraction is harvested. The PBL fractions collected are of >85% purity as determined by May-Grünwald-Giemsa-staining. Isolated PBL are stimulated to proliferate for 3 days with 4 µg/ml phytohemagglutinin (PHA; Sigma). PBL are cultured in RPMI-1640 (Life Technologies Ltd.) medium supplemented with 10% heat inactivated fetal calf serum (LifeTechnologies Ltd.) and 10 mg/ml gentamycin (Life Technologies Ltd.). After PHA stimulation the cells are cultured in medium containing 10 U/ml human recombinant IL-2 (Boehringer) until use. Viability is >95% at the point of the initiation of the experiment as determined by trypan-blue exclusion.

1.d. Determination of Cell Viability Using the MTT Assay

Cell viability is assessed by the MTT assay. In short, cells are incubated with MTT 3-(4,5-dimethylthiazol-2-yl)-2,5-diphenyltetrazollumbromide (Sigma) for 2 hours at 37° C. During this time viable cells convert MTT into water forming insoluble formazan dyes. Afterwards crystals are solubilized with a solution containing isopropanol. The OD of the supernatant is measured at 550 nm.

1.e. Determination of Cell Viability Using the WST-1 Assay

Cell viability is assessed with WST-1 assay. Cells are incubated with the tetrazolium salt WST-1 (4-[3-(4-lodophenyl)-2-(4-nitrophenyl)-2H-5-tetrazolio]-1,3-benzene disulfonate) for 2 hours at 37° C. During this time viable cells convert WST-1 into water-soluble formazan dyes. The OD of the supernatant is measured at 550 nm.

2. Materials and Methods Related to Virus Infection
2.a. Preparation of Viral Stocks HIV-1 strain Ba-L is grown to high titer in MDM. The 50% tissue culture infectious dose ($TCID_{50}$) of the virus stock is determined by endpoint dilution with serial fourfold dilutions in a 96-well microtiter plate on MDM. HIV-1 strain AT is grown to high titer in PHA-stimulated PBMC. The $TCID_{50}$ of the virus stock is determined by endpoint dilution with serial fourfold dilutions in a 96-well microtiter plate on PBMC.

2.b. HIV-1 Infection of Cells (as Determined by ELISA)

MDM, and PBMC, were incubated with HIV at a multiplicity of infection of 0.02, and 0.006 or 0.001, respectively. After two hours cells are washed to remove unbound virus and cultured for 4 to 7 days in different concentrations of the drug under investigation. On day 4, 5 and 7, 0.01 ml of supernatant is removed from the culture and virus in culture supernatant is inactivated in a final concentration of 0.05% empigen (Calbiochem-Novabiochem Co., La Jolla, Calif.). The presence of HIV-1 in the inactivated supernatant is monitored by checking for the p24-core antigen using the enzyme-linked immunosorbent assay (ELISA) system of John Moore.

3. Detection Assays to Test for the Action of the Drugs in the HIV Life Cycle 3.a. HIV-1 Infection of Cells Transfected with Different Chemokine Receptors to Study the Effect on HIV-1 Entry into the Cell The cell line HOS-CD4 and the cell lines that are derived from HOS-CD4, namely HOS-CD4-CCR2b, HOS-CD4-CCR3, HOS-CD4-CCR5 and HOS-CD4-CXCR4 are obtainable through the AIDS Research and Reference Reagent Program. These cell lines express the chemokine receptors that are used by the different HIV-1 strains and are used for investigation of the effect of compounds of above identified general formula and related compounds on their antiviral effect on the different HIV-1 strains and on modulation of these chemokine receptors. In short, cells are infected with an appropriate viral strain and the anti-viral effect of the compounds is measured by HIV p24 antigen ELISA. Furthermore, the cells are incubated with a monoclonal antibody directed against the chemokine receptor studied. Then the cells will be ished twice with phosphate-buffered saline and analyzed on a FACStar flow cytometer (Beckton Dickinson & Co., Mountain View, Calif.).

3.b. RNA PCR Detection of HIV-1 Infection to Study the Effect on the Transcriptional Level The HIV-infected cells are lysed in 1 ml TRIzol (Life Technologies Gaithersburg, Md.) and RNA is isolated according to the manufacturer's guidelines. Total RNA is dissolved in diethylpyrocarbonate (DEPC)-treated water and 1 mg of RNA is used for the synthesis of complementary DNA. The RNA is previously heated for 5 minutes at 70° C., chilled on ice and added to a mixture containing 1× reverse transcriptase (RT) buffer (Promega, Madison, Wis.), 200 U of reverse transcriptase, 0.1 M dithiothreitol (DTT, Gibco, Grand Island, N.Y.), 2.5 mM deoxynucleotidetriphosphate (dNTP's, Boehringer Mannheim, Indianapolis, Ind.), 80 U random hexamer oligonucleotides (Boehringer Mannheim) and 10 U RNAsin (Promega). The complete mixture is now incubated for 60 minutes at 37° C. and then heated for 5 minutes at 90° C. The final reaction volume is diluted 1:8 by adding distilled water. Amplification of the cDNA is accomplished using one primer biotinylated on the 5' terminal nucleotide to facilitate later capture using streptavidin. To the PCR reaction mixture the following components are added: 0.25 mM dNTP mix (Boehringer Mannheim), 1× PCR buffer (50 mM KCl, 10 mM Tris-HCl, 1.5 mM MgCl$_2$; Promega), 0.2 mM of the biotinylated HIV-1 tat/rev sense primer 5' GGC TTA GGC ATC TCC TAT GGC 3' (SEQ ID NO:1) or GAPDH sense primer 5' CCA TGG AGA AGG CTG GGG 3' (SEQ ID NO:2) and the antisense HIV-1 tat/rev primer 5' TGT CGG GTC CCC TCG TTG CTG G 3' (SEQ ID NO:3) or the antisense GAPDH primer 5' CAA AGT TGT CAT GGA TGA CC 3' (SEQ ID NO:4), 5 ml cDNA and 1 U Taq polymerase (Promega). Denaturation, annealing, and elongation temperatures for PCR are 94° C., 60° C., and 72° C. for 1, 1, and 2 min each, using a DNA thermal cycler (Perkin-Elmer, Norwalk, Conn.). Negative controls are included in each assay to confirm that none of the reagents are contaminated with cDNA or previous PCR products. PCR is also performed on RNA samples to exclude genomic DNA contamination. To confirm single band product positive reactions are subjected to 40 cycles amplification and electrophoresis followed by ethidium bromide staining. Then, for semi-qualification every primer pair is tested at different cycle numbers to determine the linear range. GAPDH mRNA levels are high and 25 cycles is enough to measure the PCR product in its linear range, whereas HIV-1 tat/rev cDNA is subjected to 38 cycles to be in the linear range, when needed. Aliquots of 5 ml of the biotinylated PCR product are semi-quantitatively analyzed using a fluorescent digoxigenin detection ELISA kit (Boehringer Mannheim) according to manufacturer's protocol. In short, the biotinylated strand of denatured PCR product is captured by immobilized streptavidin. Then, a digoxigenin labeled probe (the probe for HIV-1 tat/rev is 5' CTT TGA TAG AGA AAC TTG ATG AGT CTG 3' (SEQ ID NO:5) and the probe for GAPDH is 5' CTG CAC CAC CAA CTG CTT AGC 3' (SEQ ID NO:6)) is added followed by an alkaline phosphatase labeled antibody against digoxigenin. After addition of the substrate fluorescence is measured in relative fluorescence units (RFU) in a fluorescence multi-well plate reader (Perseptive biosystems, Framingham, Mass.) at excitation 450 nm/emission 550 nm. All data are normalized against GAPDH mRNA levels, which is used as an internal standard.

3.c. DNA PCR Detection of HIV-1 Infection to Study the Effect on the Earliest Processes of Proviral DNA Formation Trizol reagent is used for DNA isolation according to the manufacturer's protocol. In short, DNA and RNA of cell samples in trizol are isolated by chloroform. DNA is precipitated from the lower chloroform phase by 100% ethanol and the sedimented DNA is ished twice in 0.1M sodium citrate in 10% ethanol. The pellet is reconstituted in water and checked for purity by measuring the OD260/280 ratio. The earliest processes of proviral DNA formation is analyzed by checking for the formation of the HIV R/U5 product indicating that the process of reverse transcription has taken place. The R/U5 primer pair flanks sequences within the first region of viral DNA synthesized as a result of reverse transcription, this first fragment of DNA is referred to as strong-stop minus DNA. The primer set that we use detects the early steps in reverse transcription and determines whether any viral DNA is synthesized in infected cells in the presence of APHS and derivates. The method and conditions of the PCR reaction are essentially the same as described in section 3.a. The R/U5 primer pairs (Zack et al, 1990): sense 5'-GGCTAACTAGGGAACCCACTG-3' (SEQ ID NO:7) and antisense 5'-TGTGTGCCCGTCT GTTGTGTG-3' (SEQ ID NO:8) (5' end biotinylated) result in a 132bp fragment. The digoxigenin-labeled probe 5'-TGTGTGCCCGTCTGTTGTGTG-3' (SEQ ID NO:9) is used to quantify the fragment. PCR amplification conditions are denaturation at 94° C. for 5 min followed by 38 cycles of denaturation at 94° C. for 1 min, annealing at 60° C. for 1 min and extension at 72° C. for 2 min. The DNA product is finally extended at 72° C. for 10 mins. 5 ml of the amplified product is quantified using the digoxigenin-labeled probe, by means of a DIG-detection ELISA (Boehringer-Mannheim, Mannheim, Del.).

Figure 1:
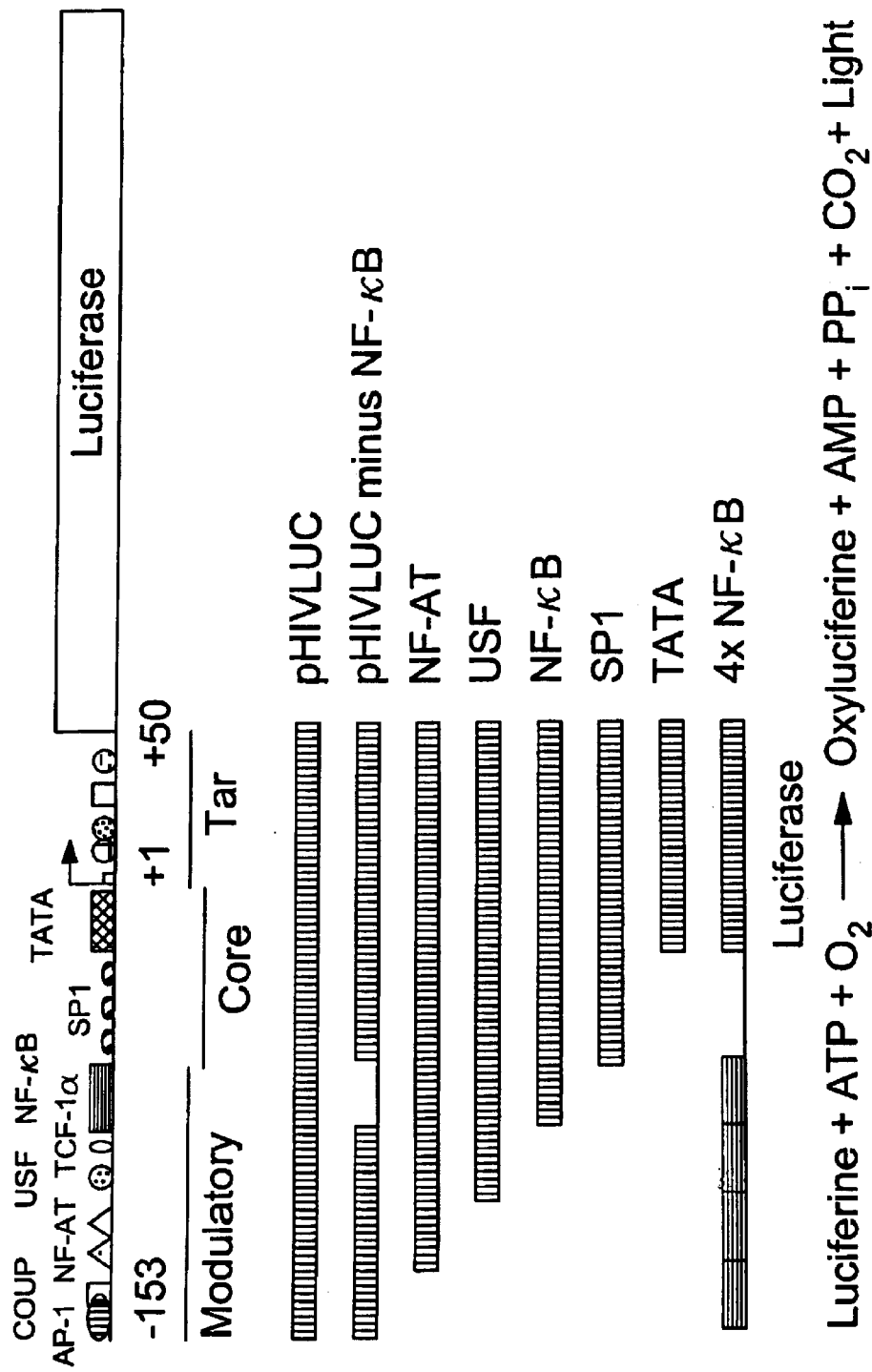
FIG. 1—Plasmids that are used for studies on the effect of compounds on HIV promoter activity.
Figure 2:
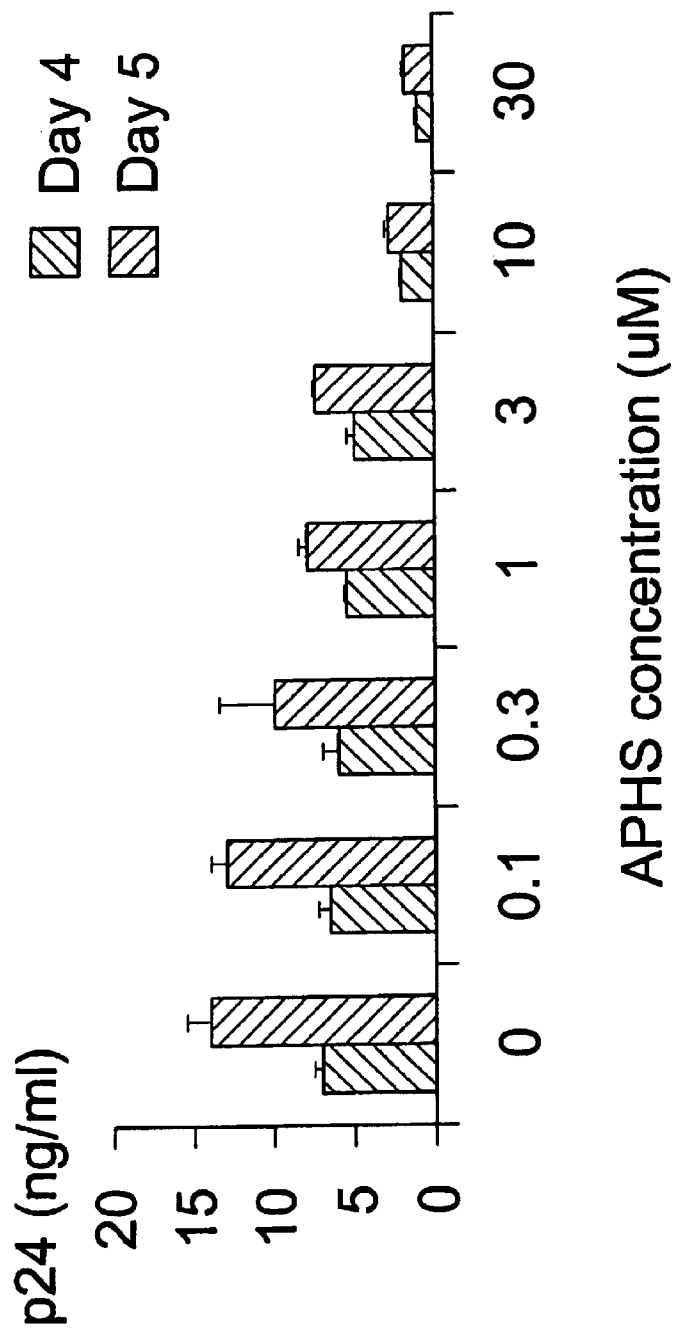
FIG. 2—Peripheral blood mononuclear cells (PBMC) were isolated from heparinized blood from HIV-1-, HIV-2-, and hepatitis B-seronegative donors and obtained on Ficoll-Hypaque density gradients. PBMC were washed twice and monocytes were purified by counter-current centrifugal elutriation. Cells were >98% monocytes by criteria of cell morphology on May-Grünwald-Giemsa-stained cytosmears and by non-specific esterase staining using alpha-naphtylacetate as substrate. Monocytes were cultured in suspension at a concentration of $2\times10^6$ cells/ml in Teflon flasks in Iscove's modified Dulbeco's medium (IMDM) with 10% heat-inactivated human AB serum negative for anti-HIV antibodies, 10 mg/ml gentamycin, and 10 mg/ml ciprofloxacin. After 7 days of incubation non-adherent monocyte-derived macrophages (MDM) were recovered from the Teflon flasks, washed and infected with HIV-$1_{Ba-L}$ at a multiplicity of infection of 0.02 for two hours. HIV-infected and mock-infected MDM's were washed twice to remove unbound virus and cultured for 4 to 7 days in different concentrations of APHS. After 4 and 5 days of incubation samples of culture supernatant were collected and p24-core antigen production was quantified using the enzyme-linked immunosorbent assay (ELISA) system of John Moore. Concentrations above 0.3 $\mu$M APHS inhibit p24 production. 30 $\mu$M APHS inhibits HIV-1 replication by 88%.

3.d. HIV-LTR Driven Luciferase Gene Expression to Study the Effect on HIV Promoter Activity pHIV-CAT constructs are obtained from the NIH AIDS Research and Reference Reagent Program (National Institute of Allergy and Infectious diseases, Rockville, Md., US). The HIV-CAT plasmids contained HindIII and BamHI restriction sites flanking the CAT gene. The HIV-long terminal repeat ("LTR") sequence is found upstream this gene. The CAT gene is excised out of the plasmid and the luciferase (LUC) gene contained in a pGL3-basic vector provided by Promega, Madison, USA) is obtained after HindIII and BamHI digestion. The LUC gene is then ligated into the empty HIV vectors, yielding HIV-LUC plasmids, with LTR-driven luciferase activity. The basic plasmid that does not contain any binding sites for eukaryotic transcription factors is pCD54 that only contains the 3' HIV-1 LTR region containing the TATA box and the TAR (where to HIV-1 tat can bind) region downstream of the LUC gene. In addition, the following plasmids are available: p3NF-kB wich contains 3 NF-kB binding sites downstream of pCD54; pCD52 which contains one binding site for SP1 downstream of pCD54; pCD23 which contains 3 SP1 binding sites and two NF-kB binding sites downstream of pCD54; pCD16 which contains one USF, one TCF-1a, two NF-kB, and three SP-1 binding sites downstream of pCD54; pCD7 which contains one NF-AT, one USF, one TCF-1a, two NF-kB, and three SP-1 binding sites downstream of pCD54; pHIV-LUC which contains the complete HIV-1 LTR region downstream of pCD54. The HIV-1 LTR consists of one AP-1 COUP, one NF-AT, one USF, one TCF-1a, two NF-kB, and three SP-1 binding sites. FIG. 1 shows the collection of plasmids that are available.

*E. coli* DH5aF' are made competent with $CaCl_2$ and are subsequently transformed with the pHIV-LUC vector and the other plasmids are described above. The plasmids are isolated from these transformants after overnight incubation.

Cells ($5 \times 10^6$ cells/ml) are transfected by electroporation with 1 mg of a plasmid expressing the LUC reporter gene, under the control of the HIV-LTR. In addition to this plasmid the cells are co-transfected with 1 mg tat plasmid as an extra transcription stimulus and 1 mg β-gal plasmid as control for transfection efficiency. After transfection, the cells are incubated at 37° C. for 2 hours in medium containing 10% FCS and 10 mg/ml gentamicin. The transfected cells are subsequently incubated with various concentrations of the drug under investigation and then stimulated by 20 ng/ml phorbol 12-myristate 13-acetate (for PBMC and PBL) or 10 mM N-acetyl-L-cysteine (for MDM). 16 hours after stimulation and compound incubation, firefly luciferase activity is measured employing the single-Luciferase™ reporter assay system (Promega, Madison, USA). β-galactosidase activity is measured 16 hours after stimulation and compound addition. The amount of activity correlates to the light emission measured by LUMAC Biocounter M2500 at 562 nm. Cells stimulated in the absence of the drug under investigation serve as control cells.

Description of Experiment with FIG. 6.

(A, B) Peripheral blood mononuclear cells (PBMC) were isolated from heparinized blood from HIV-1-, HIV-2-, and hepatitis B-seronegative donors and obtained on Ficoll-Hypaque density gradients. Cells were washed twice, stimulated with 5 μg/ml phytohemagglutinin (PHA), and cultured in RPMI-1640 medium supplemented with 5 mM Hepes, 19 mM sodium bicarbonate, 10 μg/mL gentamycin, and 10% heat-inactivated fetal calf serum (PBMC culture medium) at a concentration of $2 \times 10^6$ cells/ml. After 3 days of incubation stimulated PBMC were recovered from the flasks and infected for 2 hours with HIV-$1_{Ba-L}$ at a multiplicity of infection of 0.01. Afterwards, HIV-infected and mock-infected PBMC were washed twice to remove unbound virus. (A) PBMC were cultured at a density of $6 \times 10^5$ cells/well with different concentrations of APHS and after 5 days of incubation samples of culture supernatant were collected. (B) PBMC were cultured in suspension at a concentration of $2 \times 10^6$ cells/ml in Teflon flasks in PBMC culture medium. After 5 days of incubation PBMC were recovered from Teflon flasks, washed twice to remove unbound virus and cultured at a density of $6 \times 10^5$ PBMC/well with different concentrations of APHS. After 2 days of incubation samples of culture supernatant were collected. p24-core antigen production was quantified using the enzyme-linked immunosorbent assay (ELISA) system of John Moore. While APHS does not inhibit HIV-1 production of chronically infected PBMCs (B), APHS concentrations above 3 μM inhibit HIV-$1_{Ba-L}$ replication and 30 μM APHS inhibits HIV-1Ba-L replication even by 100% (A). (C, D) PBMC were isolated from heparinized blood from HIV-1-, HIV-2-, and hepatitis B-seronegative donors and obtained on Ficoll-Hypaque density gradients. PBMC were washed twice and monocytes were purified by counter-current centrifugal elutriation. Cells were >98% monocytes by criteria of cell morphology on May-Grünwald-Giemsa-stained cytosmears and by non-specific esterase staining using alpha-naphtylacetate as substrate. Monocytes were cultured in suspension at a concentration of $2 \times 10^6$ cells/ml in Teflon flasks in Iscove's modified Dulbeco's medium (IMDM) with 10% heat-inactivated human AB serum negative for antiviral antibodies, 10 μg/ml gentamicin, and 10 μg/ml ciprofloxacin (MDM medium). After 7 days of incubation non-adherent monocyte-derived macrophages (MDM) were recovered from the Teflon flasks, washed and infected with HIV-$1_{Ba-L}$ at a multiplicity of infection of 0.02 for two hours. Afterwards, HIV-infected and mock-infected MDM's were washed twice to remove unbound virus. (C) MDM were cultured at a density of $3 \times 10^5$ cells/well with different concentrations of APHS and after 4 days of incubation samples of culture supernatant were collected. (D) MDM were cultured in suspension at a concentration of $2 \times 10^6$ cells/ml in Teflon flasks in MDM medium. After 5 days of incubation MDM were recovered from Teflon flasks, washed twice to remove unbound virus and cultured at a density of $3 \times 10^5$ cells/well with different concentrations of APHS. After 2 days of incubation samples of culture supernatant were collected. p24-core antigen production was quantified using the enzyme-linked immunosorbent assay (ELISA) system of John Moore. While APHS does not inhibit HIV-1 production by chronically infected MDM (D), concentrations above 3 μM APHS inhibit p24 production by acutely infected MDM. 30 μM APHS inhibits HIV-1 replication by 88% (C). The results shown in A–D are representative of three independent PBMC donors. These results suggest that APHS inhibits the early steps of the HIV-1 life cycle and that it is for instance not a protease inhibitor.

Description of Experiment with FIG. 7

Monocyte-derived macrophages (MDM) were obtained like described above. MDM were then washed twice and cultured for 4 to 7 days in different concentrations of APHS. After a 4 days incubation period cellular viability was assessed by MTT cytotoxicity assay where viable cells convert MTT into a colored formazan dye that can be measured spectrophotometrically.

Description of Experiment with FIG. 8

U1 cells, chronically infected U937 cells that harbour two copies of the HIV-1IIIb strain genome in their cellular genome and don't produce viral particles, were stimulated with 100 ng/ml phorbol 12-myristate 13-acetate (PMA) for 30 min. PMA treatment of U1 cells is known to trigger transcription of the HIV-1 genome and therefore the production of infectious particles. Afterwards cells were washed and cultured at a density of $1 \times 10^6$ cells/well with different concentrations of APHS and related compounds (LM-3142, LM-3155 and LM-3189). As a negative control some cells were incubated with 30 μM N-acetyl-L-cysteine (NAC) which is known to block PMA effect (data not shown).

Furthermore, APHS activity was tested with drug-resistant HIV strains (Table 2). Surprisingly, the inhibitory activity against otherwise drug resistant strains was high, sometimes even two- to four-fold higher than the activity against a sensitive strain.

FIG. 9—Structure of a compound described herein.

FIG. 10—The 50% inhibitory concentration (IC$_{50}$) of the compounds APHS, LM-3177, LM-3189, LM-3142, LM-3155 and aspirin that suppresses HIV-1 replication in primary human peripheral blood mononuclear cells. The infection was performed as described with FIG. 6. The IC50 values are depicted in micromolars. The letters X, Y, Z, A, B, D, E in the first row (upper line) refer to the same letters in the general formula of the compound in FIG. 9.

FIG. 11—Selected chemical structures for letters X, Y, Z, A, B, D, E in the general formula of the compound in FIG. 9. Of particular interest are the combinations in these letters wherein Z=H, Y=S, E=CH$_2$C≡C(CH$_2$)$_3$CH$_3$, X=O, B=-, D=-, and A is either CH$_3$, CH$_2$CH$_3$, CH$_2$CH$_2$CH$_3$, CH$_2$(CH$_2$)$_2$CH$_3$, CH$_2$(CH$_2$)$_3$CH$_3$, CH$_2$(CH$_2$)$_4$CH$_3$, CH$_2$(CH$_2$)$_5$CH$_3$, or CH$_2$(CH$_2$)$_6$CH$_3$ and the combinations in letters wherein Z=H, Y=S, E=C(CH$_3$)$_3$, X=O, A=C, B=O, and D=CH$_3$ and the combinations wherein Z=H, Y=S, E=C(CH$_3$)$_3$, X=-, A=C, B=O, and D=CH$_3$ and the combinations wherein Z=SC(CH$_3$)$_3$, Y=-, E=-, X=O, A=C, B=O, and D=CH$_3$ and the combinations wherein Z=SC(CH$_3$)$_3$, Y=-, E=-, X=-, A=C, B=O, and D=CH$_3$ and the combinations wherein Y=-, E=-, Z=SCH$_2$C≡C(CH$_2$)$_3$CH$_3$, X=O, B=-, D=-, and A is either CH$_3$, CH$_2$CH$_3$, CH$_2$CH$_2$CH$_3$, CH$_2$(CH$_2$)$_2$CH$_3$, CH$_2$(CH$_2$)$_3$CH$_3$, CH$_2$(CH$_2$)$_4$CH$_3$, CH$_2$(CH$_2$)$_5$CH$_3$, or CH$_2$(CH$_2$)$_6$CH$_3$.

TABLE 1

Antiretroviral agents (approved or in advanced development).

Nucleoside analogue reverse transcriptase inhibitors

Zidovudine (ZDV, AZT)
Didanosine (ddI)
Zalcitabine (ddC)
Stavudine (d4T)
Lamivudine (3TC)
Abacavir (1592U89)

Non-nucleoside reverse transcriptase inhibitors

Nevirapine
Delavirdine
Efavirenz (DMP-266)

TABLE 1-continued

Antiretroviral agents (approved or in advanced development).

Nucleotide analogue reverse transcriptase inhibitors

Adefovir dipivoxil

Protease inhibitors

Saquinavir
Ritonavir
Indinavir
Nelfinavir
Amprenavir (141W94, VX-478)

TABLE 2

IC50 values of APHS for drug-resistant HIV-1 strains

| Virus | Resistance | IC50 of APHS (in M) |
|---|---|---|
| HXB2* | — | 12.6 +/- 2.3 |
| 41 + 215Y** | AZT | 5.1 +/- 1.9 |
| 184V*** | 3TC | 4.5 +/- 1.1 |
| 3096**** | High***** | 4.1 +/- 1.0 |
| 4602****** | Ritonavir | 5.2 |

HXB2 is the molecular clone of the first laboratory HIV-1 isolate. The genes that contain the drug-resistance mutations are excised from the clinical isolates and cloned into the genetic background of HXB2. Thus all tested HIV-1 strains have the same genetic background.
**41 + 215Y is a AZT-resistant HIV-1 strain (1).
***184V is a 3TC-resistant HIV-1 strain as described by Schuurman et al (2).
****Strain 3096 is a RT inhibitor resistant HIV-1 strain as described by de Jong et al (3). This strain contains an insertion of two amino acids between codons 68 and 69 of RT as well as an amino-acid change at codon 67.
*****Phenotypic resistance analysis showed high levels of resistance to zidovudine, lamivudine and stavudine (in all patients tested) and moderate levels of resistance to didanosine and zalcitabine (in two patients).
******Strain 4602 is a HIV protease resistant HIV-1 strain as described by Nijhuis et al. It contains the following mutations: 36I, 54V, 71V, and 77M (4).

TABLE 3

IC50 and toxicity determinations of an anti-viral as provided herein.
Side group references are as in FIG. 9.

| | X | Y | Z | A | B | D | Y | E | IC$_{50}$* | not toxic at* |
|---|---|---|---|---|---|---|---|---|---|---|
| APHS | O | S | H | C | O | CH$_3$ | S | CH$_2$C C(CH$_2$)$_3$CH$_3$ | 10 | 30 |
| BPHS | S | O | H | CH$_2$ | — | C C(CH$_2$)$_3$CH$_3$ | O | (CH$_2$)$_3$CH$_3$ | 40 | 30 |
| c1 | O | S | H | C$_2$H$_5$ | — | — | S | CH$_2$C C(CH$_2$)$_3$CH$_3$ | 40 | 30 |
| c2 | O | S | H | C | O | CH$_3$ | S | (CH$_2$)$_5$CO$_2$H | 15 | 30 |
| c3 | O | S | H | C | O | CH$_3$ | S | (CH$_2$)$_3$O(CH$_2$)$_2$CH$_3$ | 0.3 | 30 |
| c4 | O | S | H | H | — | — | S | (CH$_2$)$_5$CO$_2$H | 30 | 100 |
| c5 | O | S | H | H | — | — | S | (CH$_2$)3O(CH$_2$)$_2$CH$_3$ | 10 | 10 |
| c7 | O | S | H | C | O | CF$_3$ | S | (CH$_2$)3O(CH$_2$)$_2$CH$_3$ | 0.3 | 10 |

*all concentrations are in micromolar

References

1. Differences in resistance contribute more strongly to the evolution of zidovudine resistance in HIV-1 infected patients than differences in replication capacity.
2. Schuurman R, Nijhuis M, van Leeuwen R, Schipper P, de Jong D, Collis P, Danner S A, Mulder J, Loveday C, Christopherson C, Kwok S, Sninsky J, Boucher C A. Rapid changes in human immunodeficiency virus type 1 RNA load and appearance of drug-resistant virus populations in persons treated with lamivudine (3TC).J. Infect. Dis. 1995; 171:1411–1419.
3. de Jong J J, Goudsmit J, Lukashov V V, Hillebrand, M E, Baan E, Huismans R, Danner S A, ten Veen J H, de Wolf F, Jurriaans S. Insertion of two amino acids combined with changes in reverse transcriptase containing tyrosine-215 of HIV-1 resistant to multiple nucleoside analogs. AIDS 1999; 13:75-80.
4. Nijhuis M, Schuurman R, de Jong D, Erickson J, Gustchina E, Albert J, Schipper P, Gulnik S, Boucher C A. Increased fitness of drug resistant HIV-1 protease as a result of acquisition of compensatory mutations during suboptimal therapy. AIDS 1999;13:2349-59.

What is claimed is:

1. A method for treating a viral infection in an animal or a human subject suffering therefrom with a first antiviral agent, said method comprising: administering to the subject the first antiviral agent wherein said first antiviral agent comprises a compound of the general formula

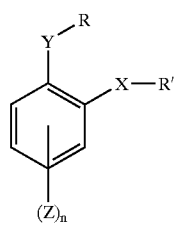

wherein X and Y are independently selected from the group consisting of O, S, SO, $SO_2$, and $SO_3$; wherein n is 0, 1, 2, 3, 4;

wherein R, and R' are independently H, with the proviso that when R is H, R' is not H, and is selected from the group consisting of H, $CH_3$, $CF_3$, $CH_2Cl$, $CH_2Br$, $CH_2CH_3$, $(CH_2)_2CH_3$, $(CH_2)_3CH_3$, $(CH_2)_4CH_3$, $(CH_2)_5 CH_3$, $(CH_2)_6CH_3$, $CH(CH_3)_2$, $CH(CH_3)_3$, $CH=C=CH_2$, $(CH_2)_2O(CH_2)_3CH_3$, $CH_2HC=CH(CH_2)_3CH_3$, $CH_2C\equiv C(CH_2)_3CH_3$, $CH_2C\equiv C(CH_2)_2CH_3$, $CH_2C\equiv CCH_2CH_3$, $CH_2C\equiv CCH_3$ and $CH_2C\equiv CH$ and isomers or homologues thereof; and Z is independently R, R', XR, XR', YR or YR'.

2. The method according to claim 1 wherein the viral infection is of retroviral origin.

3. The method according to claim 1 wherein the viral infection is caused by a virus at least partially resistant to a second antiviral agent selected from the group consisting of zidovudine, didanosine, zalcitabine, stayudine, larniyudine, ritonavir and mixtures thereof.

4. The method according to any claim 1 further comprising administering to the subject another pharmaceutical composition selected from the group consisting of amantadine, rimanditine, acyclovir, gangcyclovir, foscarnet, ribavirine, zidovudine, didanosine, zalcitabine, stavudine, lamivudine, abacavir, nevirapine, delavirdine, efavirenz, adefovir dipivoxil, saquinavir, ritonavir, indinavir, nelfinavir, amprenavir and mixtures thereof.

5. The method according to claim 2 further comprising administering to the subject another pharmaceutical composition selected from the group consisting of amantadine, rimanditine, acyclovir, gangcyclovir, foscamet, ribavirine, zidovudine, didanosine, zalcitabine, stavudine, lamivudine, abacavir, nevirapine, delavirdine, eEfavirenz, adefovir dipivoxil, saquinavir, ritonavir, indinavir, nelfinavir, amprenavir and mixtures thereof.

6. The method according to claim 3 further comprising administering to the subject another pharmaceutical composition selected from the group consisting of amantadine, rimanditinc, acyclovir, gangcyclovir, foscamet, ribavirine, abacavir, nevirapine, delavirdine, efavirenz, adefovir dipivoxil, saguinavir, indinavir, nelfinavir, amprenavir and mixtures thereof.

* * * * *

SEQUENCE LISTING

<160> NUMBER OF SEQ ID NOS: 9

<210> SEQ ID NO 1
<211> LENGTH: 21
<212> TYPE: DNA
<213> ORGANISM: Artificial Sequence
<220> FEATURE:
<223> OTHER INFORMATION: Primer: HIV 1 tat/rev sense primer

<400> SEQUENCE: 1
ggcttaggca tctcctatgg c                                              21

<210> SEQ ID NO 2
<211> LENGTH: 18
<212> TYPE: DNA
<213> ORGANISM: Artificial Sequence
<220> FEATURE:
<223> OTHER INFORMATION: Primer: GAPDH sense primer

<400> SEQUENCE: 2
ccatggagaa ggctgggg                                                  18

<210> SEQ ID NO 3
<211> LENGTH: 22
<212> TYPE: DNA
<213> ORGANISM: Artificial Sequence
<220> FEATURE:
<223> OTHER INFORMATION: Primer: antisense GAPDH primer

<400> SEQUENCE: 3
tgtcgggtcc cctcgttgct gg                                             22

<210> SEQ ID NO 4
<211> LENGTH: 20
<212> TYPE: DNA
<213> ORGANISM: Artificial Sequence
<220> FEATURE:
<223> OTHER INFORMATION: Primer: antisense GAPDH primer

<400> SEQUENCE: 4
caaagttgtc atggatgacc                                                20

<210> SEQ ID NO 5
<211> LENGTH: 27
<212> TYPE: DNA
<213> ORGANISM: Artificial Sequence
<220> FEATURE:
<223> OTHER INFORMATION: Probe for HIV-1 tat/rev

<400> SEQUENCE: 5
ctttgataga gaaacttgat gagtctg                                        27

```
<210> SEQ ID NO 6
<211> LENGTH: 21
<212> TYPE: DNA
<213> ORGANISM: Artificial Sequence
<220> FEATURE:
<223> OTHER INFORMATION: Probe for GAPDH

<400> SEQUENCE: 6
ctgcaccacc aactgcttag c                                              21

<210> SEQ ID NO 7
<211> LENGTH: 21
<212> TYPE: DNA
<213> ORGANISM: Artificial Sequence
<220> FEATURE:
<223> OTHER INFORMATION: Primer: R/U5 primer

<400> SEQUENCE: 7
ggctaactag ggaacccact g                                              21

<210> SEQ ID NO 8
<211> LENGTH: 21
<212> TYPE: DNA
<213> ORGANISM: Artificial Sequence
<220> FEATURE:
<223> OTHER INFORMATION: Primer: antisense R/U5 primer

<400> SEQUENCE: 8
tgtgtgcccg tctgttgtgt g                                              21

<210> SEQ ID NO 9
<211> LENGTH: 21
<212> TYPE: DNA
<213> ORGANISM: Artificial Sequence
<220> FEATURE:
<223> OTHER INFORMATION: Probe: digoxigenin-labeled probe

<400> SEQUENCE: 9
tgtgtgcccg tctgttgtgt g                                              21
```